US008025896B2

(12) United States Patent
Malaviya et al.

(10) Patent No.: US 8,025,896 B2
(45) Date of Patent: *Sep. 27, 2011

(54) POROUS EXTRACELLULAR MATRIX SCAFFOLD AND METHOD

(75) Inventors: Prasanna Malaviya, Ft. Wayne, IN (US); Herbert E. Schwartz, Ft. Wayne, IN (US); Pamela L. Plouhar, South Bend, IN (US); Mark J. Pelo, Macy, IN (US)

(73) Assignee: DePuy Products, Inc., Warsaw, IN (US)

( * ) Notice: Subject to any disclaimer, the term of this patent is extended or adjusted under 35 U.S.C. 154(b) by 1172 days.

This patent is subject to a terminal disclaimer.

(21) Appl. No.: 10/195,354

(22) Filed: Jul. 15, 2002

(65) Prior Publication Data

US 2003/0044444 A1    Mar. 6, 2003

Related U.S. Application Data

(60) Provisional application No. 60/305,786, filed on Jul. 16, 2001, provisional application No. 60/388,761, filed on Jun. 14, 2002.

(51) Int. Cl.
*A61F 2/00* (2006.01)
(52) U.S. Cl. ........................ 424/423; 424/422
(58) Field of Classification Search .................. 424/423, 424/426; 623/11.11
See application file for complete search history.

(56) References Cited

U.S. PATENT DOCUMENTS

| | | | |
|---|---|---|---|
| 3,272,204 A | 9/1966 | Artandl et al. | |
| 3,562,820 A | 2/1971 | Braun | |
| 4,105,034 A | 8/1978 | Shalaby et al. | |
| 4,130,639 A | 12/1978 | Shalaby et al. | |
| 4,140,678 A | 2/1979 | Shalaby et al. | |
| 4,141,087 A | 2/1979 | Shalaby et al. | |
| 4,205,399 A | 6/1980 | Shalaby et al. | |
| 4,208,511 A | 6/1980 | Shalaby et al. | |
| 4,352,463 A | 10/1982 | Baker | |
| 4,400,833 A | 8/1983 | Kurland | |
| 4,418,691 A | 12/1983 | Yannas et al. | |
| 4,585,458 A | 4/1986 | Kurland | |
| 4,610,397 A * | 9/1986 | Fischer et al. | 241/86 |
| 4,642,120 A | 2/1987 | Nevo et al. | |
| 4,669,473 A | 6/1987 | Richards et al. | |
| 4,703,108 A * | 10/1987 | Silver et al. | 530/356 |
| 4,705,040 A | 11/1987 | Mueller et al. | |
| 4,741,330 A | 5/1988 | Hayhurst | |
| 4,750,492 A | 6/1988 | Jacobs | |
| 4,846,835 A | 7/1989 | Grande | |
| 4,873,976 A | 10/1989 | Schreiber | |
| 4,880,429 A | 11/1989 | Stone | |
| 4,902,508 A | 2/1990 | Badylak et al. | |
| 4,919,667 A | 4/1990 | Richmond | |
| 4,956,178 A | 9/1990 | Badylak et al. | |
| 4,956,179 A | 9/1990 | Bamberg et al. | |
| 4,976,715 A | 12/1990 | Bays et al. | |
| 5,007,934 A | 4/1991 | Stone | |
| 5,061,286 A | 10/1991 | Lyle | |
| 5,102,421 A | 4/1992 | Anspach, Jr. | |
| 5,108,438 A | 4/1992 | Stone | |
| 5,128,326 A | 7/1992 | Balazs et al. | |
| RE34,021 E | 8/1992 | Mueller et al. | |
| 5,236,431 A | 8/1993 | Gogolewski et al. | |
| 5,246,441 A | 9/1993 | Ross et al. | |
| 5,258,015 A | 11/1993 | Li et al. | |
| 5,269,809 A | 12/1993 | Hayhurst et al. | |
| 5,275,826 A | 1/1994 | Badylak et al. | |
| 5,281,422 A | 1/1994 | Badylak et al. | |
| 5,306,311 A | 4/1994 | Stone et al. | |
| 5,320,633 A | 6/1994 | Allen et al. | |
| 5,329,846 A | 7/1994 | Bonutti | |
| 5,350,583 A | 9/1994 | Yoshizato et al. | |
| 5,352,463 A | 10/1994 | Badylak et al. | |
| 5,372,821 A | 12/1994 | Badylak et al. | |
| 5,374,268 A | 12/1994 | Sander | |
| 5,376,118 A | 12/1994 | Kaplan et al. | |
| 5,380,334 A | 1/1995 | Torrie et al. | |
| 5,445,833 A | 8/1995 | Badylak et al. | |
| 5,447,940 A | 9/1995 | Harvey et al. | |
| 5,460,962 A | 10/1995 | Kemp | |
| 5,464,929 A | 11/1995 | Bezwada et al. | |
| 5,479,033 A | 12/1995 | Baca et al. | |
| 5,514,181 A | 5/1996 | Light et al. | |
| 5,516,533 A | 5/1996 | Badylak et al. | |
| 5,520,691 A | 5/1996 | Branch | |

(Continued)

FOREIGN PATENT DOCUMENTS

EP        0 446 105 A2    1/1992

(Continued)

OTHER PUBLICATIONS

Answers.com definition of "freeze-dry", accessed May 12, 2005. 6 pages.*
Definitions of "intertwine" and "twine": American Heritage Dictionary of the English Language Online. Accessed Sep. 29, 2005. 2 pages.*
How to Cut Meat Products. 2001. Urschel Corp. Accessed online at fr.urschel.com/literature/HTCMeat.pdf on Oct. 3, 2005. 8 pages.*
Merriam-Webster Online Dictionary definitions of "suspension," "suspend," "cohesive," and "cohesion." Accessed Mar. 29, 2006. 5 pages.*

(Continued)

*Primary Examiner* — L E Barnhart
(74) *Attorney, Agent, or Firm* — Barnes & Thornburg LLP

(57) ABSTRACT

A method of making an implantable scaffold for repairing damaged or diseased tissue includes the step of suspending pieces of an extracellular matrix material in a liquid. The extracellular matrix material and the liquid are formed into a mass. The liquid is subsequently driven off so as to form interstices in the mass. Porous implantable scaffolds fabricated by such a method are also disclosed.

10 Claims, 8 Drawing Sheets

U.S. PATENT DOCUMENTS

| | | | |
|---|---|---|---|
| 5,545,178 A | 8/1996 | Kensey et al. |
| 5,554,389 A | 9/1996 | Badylak et al. |
| 5,569,252 A | 10/1996 | Justin et al. |
| 5,573,784 A | 11/1996 | Badylak et al. |
| 5,591,234 A | 1/1997 | Kirsch |
| 5,593,441 A | 1/1997 | Lichtenstein et al. |
| 5,595,621 A | 1/1997 | Light et al. |
| 5,595,751 A | 1/1997 | Bezwada et al. |
| 5,597,579 A | 1/1997 | Bezwada et al. |
| 5,601,558 A | 2/1997 | Torrie et al. |
| 5,607,687 A | 3/1997 | Bezwada et al. |
| 5,618,552 A | 4/1997 | Bezwada et al. |
| 5,620,698 A | 4/1997 | Bezwada et al. |
| 5,626,614 A | 5/1997 | Hart |
| 5,630,824 A | 5/1997 | Hart |
| 5,632,745 A | 5/1997 | Schwartz |
| 5,641,518 A | 6/1997 | Badylak et al. |
| 5,645,850 A | 7/1997 | Bezwada et al. |
| 5,645,860 A | 7/1997 | Knapp, Jr. et al. |
| 5,648,088 A | 7/1997 | Bezwada et al. |
| 5,660,225 A | 8/1997 | Saffran |
| 5,668,288 A | 9/1997 | Storey et al. |
| 5,669,912 A | 9/1997 | Spetzler |
| 5,677,355 A | 10/1997 | Shalaby et al. |
| 5,681,353 A | 10/1997 | Li et al. |
| 5,693,085 A | 12/1997 | Bulrge et al. |
| 5,695,998 A | 12/1997 | Badylak et al. |
| 5,698,213 A | 12/1997 | Jamiolkowski et al. |
| 5,700,583 A | 12/1997 | Jamiolkowski et al. |
| 5,702,462 A | 12/1997 | Oberlander |
| 5,711,960 A | 1/1998 | Shikinami |
| 5,711,969 A * | 1/1998 | Patel et al. ............ 424/551 |
| 5,725,556 A | 3/1998 | Moser et al. |
| 5,730,933 A | 3/1998 | Peterson |
| 5,733,337 A | 3/1998 | Carr, Jr. et al. |
| 5,733,868 A | 3/1998 | Peterson et al. |
| 5,735,897 A | 4/1998 | Bulrge |
| 5,735,903 A | 4/1998 | Li et al. |
| 5,736,372 A | 4/1998 | Vacanti et al. |
| 5,753,267 A | 5/1998 | Badylak et al. |
| 5,755,791 A | 5/1998 | Whitson et al. |
| 5,759,190 A | 6/1998 | Vibe-Hansen et al. |
| 5,759,205 A | 6/1998 | Valentini |
| 5,762,600 A | 6/1998 | Bruchman et al. |
| 5,762,966 A | 6/1998 | Knapp et al. |
| 5,769,899 A | 6/1998 | Schwartz et al. |
| 5,773,577 A | 6/1998 | Cappello |
| 5,788,625 A | 8/1998 | Plouhar et al. |
| 5,795,353 A | 8/1998 | Felt |
| 5,800,537 A | 9/1998 | Bell |
| 5,830,708 A | 11/1998 | Naughton |
| 5,834,232 A | 11/1998 | Bishop et al. |
| 5,842,477 A | 12/1998 | Naughton et al. |
| 5,847,012 A | 12/1998 | Shalaby et al. |
| 5,855,610 A | 1/1999 | Vacanti et al. |
| 5,855,613 A | 1/1999 | Antanavich et al. |
| 5,855,619 A | 1/1999 | Caplan et al. |
| 5,859,150 A | 1/1999 | Jamiolkowski et al. |
| 5,861,004 A | 1/1999 | Kensey et al. |
| 5,863,551 A | 1/1999 | Woerly |
| 5,866,165 A | 2/1999 | Liu et al. |
| 5,866,414 A | 2/1999 | Badylak et al. |
| 5,885,619 A | 3/1999 | Patel et al. |
| 5,891,558 A | 4/1999 | Bell et al. |
| 5,899,939 A | 5/1999 | Boyce et al. |
| 5,906,997 A | 5/1999 | Schwartz et al. |
| 5,916,265 A | 6/1999 | Hu |
| 5,922,028 A | 7/1999 | Plouhar et al. |
| 5,939,323 A | 8/1999 | Valentini et al. |
| 5,948,429 A | 9/1999 | Bell et al. |
| 5,954,723 A | 9/1999 | Spetzler |
| 5,954,747 A | 9/1999 | Clark |
| 5,955,100 A | 9/1999 | Bosslet et al. |
| 5,958,874 A | 9/1999 | Clark et al. |
| 5,968,096 A | 10/1999 | Whitson et al. |
| 5,969,020 A | 10/1999 | Shalaby et al. |
| 5,971,987 A | 10/1999 | Huxel et al. |
| 5,980,524 A | 11/1999 | Justin et al. |
| 5,981,802 A | 11/1999 | Katz |
| 5,981,825 A | 11/1999 | Brekke |
| 5,989,269 A | 11/1999 | Vibe-Hansen et al. |
| 5,989,280 A | 11/1999 | Euteneuer et al. |
| 5,993,475 A | 11/1999 | Lin et al. |
| 5,993,844 A | 11/1999 | Abraham et al. |
| 5,997,575 A | 12/1999 | Whitson et al. |
| 6,010,525 A | 1/2000 | Bonutti et al. |
| 6,017,301 A | 1/2000 | Schwartz et al. |
| 6,017,348 A | 1/2000 | Hart et al. |
| 6,027,744 A | 2/2000 | Vacanti et al. |
| 6,034,140 A | 3/2000 | Schwartz et al. |
| 6,042,610 A | 3/2000 | Li et al. |
| 6,051,750 A | 4/2000 | Bell |
| 6,056,752 A | 5/2000 | Roger |
| 6,056,777 A | 5/2000 | McDowell |
| 6,056,778 A | 5/2000 | Grafton et al. |
| 6,060,640 A | 5/2000 | Pauley et al. |
| 6,066,160 A | 5/2000 | Colvin et al. |
| 6,068,648 A | 5/2000 | Cole et al. |
| 6,077,989 A | 6/2000 | Kandel et al. |
| 6,080,194 A | 6/2000 | Pachence et al. |
| 6,093,201 A | 7/2000 | Cooper et al. |
| 6,098,347 A | 8/2000 | Jaeger et al. |
| 6,099,567 A | 8/2000 | Badylak et al. |
| 6,110,212 A | 8/2000 | Gregory |
| 6,126,686 A | 10/2000 | Badylak et al. |
| 6,133,325 A | 10/2000 | Schwartz et al. |
| 6,146,385 A | 11/2000 | Torrie et al. |
| 6,152,935 A | 11/2000 | Kammerer et al. |
| 6,153,292 A | 11/2000 | Bell et al. |
| 6,156,044 A | 12/2000 | Kammerer et al. |
| 6,165,225 A | 12/2000 | Antanavich et al. |
| 6,171,344 B1 | 1/2001 | Atala |
| 6,176,880 B1 | 1/2001 | Plouhar et al. |
| 6,179,840 B1 | 1/2001 | Bowman |
| 6,179,872 B1 | 1/2001 | Bell et al. |
| 6,187,039 B1 | 2/2001 | Hiles et al. |
| 6,197,296 B1 | 3/2001 | Davies et al. |
| 6,206,931 B1 | 3/2001 | Cook et al. |
| 6,214,047 B1 | 4/2001 | Melvin |
| 6,214,048 B1 | 4/2001 | Ito et al. |
| 6,214,049 B1 | 4/2001 | Gayer et al. |
| 6,224,892 B1 | 5/2001 | Searle |
| 6,235,057 B1 | 5/2001 | Roger et al. |
| 6,242,247 B1 | 6/2001 | Rieser et al. |
| 6,251,143 B1 | 6/2001 | Schwartz et al. |
| 6,251,876 B1 | 6/2001 | Bellini et al. |
| 6,264,702 B1 | 7/2001 | Ory et al. |
| 6,265,333 B1 | 7/2001 | Dzenis et al. |
| 6,267,957 B1 | 7/2001 | Green et al. |
| 8,258,124 | 7/2001 | Darois at al. |
| 6,270,530 B1 | 8/2001 | Eldridge et al. |
| 6,273,893 B1 | 8/2001 | McAllen, III et al. |
| 6,280,473 B1 | 8/2001 | Lemperle et al. |
| 6,280,474 B1 | 8/2001 | Cassidy et al. |
| 6,283,980 B1 | 9/2001 | Vibe-Hansen et al. |
| 6,288,043 B1 | 9/2001 | Spiro et al. |
| 6,290,711 B1 | 9/2001 | Caspari et al. |
| 6,293,961 B2 | 9/2001 | Schwartz et al. |
| 6,294,041 B1 | 9/2001 | Boyce et al. |
| 6,299,905 B1 | 10/2001 | Peterson et al. |
| 6,306,156 B1 | 10/2001 | Clark |
| 6,306,159 B1 | 10/2001 | Schwartz et al. |
| 6,306,177 B1 | 10/2001 | Felt et al. |
| 6,319,258 B1 | 11/2001 | McAllen, III et al. |
| 6,319,271 B1 | 11/2001 | Schwartz et al. |
| 6,326,025 B1 | 12/2001 | Sigler et al. |
| 6,333,029 B1 | 12/2001 | Vyakarnam et al. |
| 6,334,872 B1 | 1/2002 | Termin et al. |
| 6,355,699 B1 | 3/2002 | Vyakarnam et al. |
| 6,358,284 B1 | 3/2002 | Fearnot et al. |
| 6,364,884 B1 | 4/2002 | Bowman et al. |
| 6,371,958 B1 | 4/2002 | Overaker |
| 6,373,221 B1 | 4/2002 | Koike et al. |
| 6,379,367 B1 | 4/2002 | Vibe-Hansen et al. |
| 6,379,710 B1 | 4/2002 | Badylak |
| 6,383,221 B1 | 5/2002 | Scarborough et al. |
| 6,387,693 B2 | 5/2002 | Rieser et al. |

| | | |
|---|---|---|
| 6,409,764 B1 | 6/2002 | White et al. |
| 6,423,073 B2 | 7/2002 | Bowman |
| 6,436,110 B2 | 8/2002 | Bowman et al. |
| 6,440,444 B2 | 8/2002 | Boyce et al. |
| 6,447,517 B1 | 9/2002 | Bowman |
| 6,451,032 B1 | 9/2002 | Ory et al. |
| 6,458,158 B1 | 10/2002 | Anderson et al. |
| 6,458,383 B2 | 10/2002 | Chen et al. |
| 6,464,729 B1 | 10/2002 | Kandel |
| 6,497,650 B1 | 12/2002 | Nicolo |
| 6,497,707 B1 | 12/2002 | Bowman et al. |
| 6,508,821 B1 | 1/2003 | Schwartz et al. |
| 6,517,564 B1 | 2/2003 | Grafton et al. |
| 6,566,345 B2 | 5/2003 | Miller et al. |
| 6,572,650 B1 | 6/2003 | Abraham et al. |
| 6,592,623 B1 | 7/2003 | Bowlin et al. |
| 6,596,296 B1 | 7/2003 | Nelson et al. |
| 6,638,312 B2 | 10/2003 | Plouhar et al. |
| 6,652,872 B2 | 11/2003 | Nevo et al. |
| 6,666,892 B2 | 12/2003 | Hiles et al. |
| 6,692,499 B2 | 2/2004 | Törmäläet et al. |
| 6,812,221 B2 | 11/2004 | McKeehan et al. |
| 6,840,962 B1 | 1/2005 | Vacanti et al. |
| 6,869,938 B1 | 3/2005 | Schwartz et al. |
| 6,989,034 B2 | 1/2006 | Hammer et al. |
| 2001/0002446 A1 | 5/2001 | Plouhar et al. |
| 2001/0023373 A1 | 9/2001 | Plouhar et al. |
| 2001/0024658 A1 | 9/2001 | Chen et al. |
| 2001/0043943 A1 | 11/2001 | Coffey |
| 2002/0019649 A1 | 2/2002 | Sikora et al. |
| 2002/0031551 A1 | 3/2002 | Peterson et al. |
| 2002/0034533 A1 | 3/2002 | Peterson et al. |
| 2002/0038151 A1 | 3/2002 | Plouhar et al. |
| 2002/0048595 A1 | 4/2002 | Geistlich et al. |
| 2002/0052628 A1 | 5/2002 | Bowman |
| 2002/0090725 A1 | 7/2002 | Simpson et al. |
| 2002/0091444 A1 | 7/2002 | Yang |
| 2002/0095157 A1 | 7/2002 | Bowman |
| 2002/0099448 A1 | 7/2002 | Hiles |
| 2002/0131989 A1 | 9/2002 | Brown et al. |
| 2002/0165611 A1 | 11/2002 | Enzerink et al. |
| 2002/0169465 A1 | 11/2002 | Bowman et al. |
| 2002/0173806 A1 | 11/2002 | Giannetti et al. |
| 2003/0014126 A1* | 1/2003 | Patel et al. ............... 623/23.72 |
| 2003/0021827 A1 | 1/2003 | Malaviya et al. |
| 2003/0023316 A1 | 1/2003 | Brown et al. |
| 2003/0032961 A1* | 2/2003 | Pelo et al. ..................... 606/72 |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0044444 A1 | 3/2003 | Malaviya et al. |
| 2003/0049299 A1 | 3/2003 | Malaviya et al. |
| 2003/0078617 A1 | 4/2003 | Schwartz et al. |
| 2003/0212447 A1 | 11/2003 | Euteneuer et al. |
| 2004/0059431 A1 | 3/2004 | Plouhar et al. |
| 2004/0143344 A1 | 7/2004 | Malaviya et al. |
| 2004/0166169 A1 | 8/2004 | Malaviya et al. |
| 2004/0220574 A1 | 11/2004 | Pelo et al. |
| 2005/0027307 A1 | 2/2005 | Schwartz et al. |
| 2005/0249771 A1 | 11/2005 | Malaviya et al. |
| 2005/0249772 A1 | 11/2005 | Malaviya et al. |

FOREIGN PATENT DOCUMENTS

| | | |
|---|---|---|
| EP | 0591991 A2 | 4/1994 |
| EP | 0632999 A1 | 11/1995 |
| EP | 0 734 736 A1 | 10/1996 |
| EP | 1070487 | 1/2001 |
| EP | 1593400 A1 | 11/2005 |
| FR | 2422386 | 4/1978 |
| GB | 606427 | 8/1948 |
| GB | 805843 | 12/1958 |
| GB | 968840 | 9/1964 |
| GB | 2 215 209 | 9/1989 |
| JP | 11319068 A | 11/1999 |
| WO | WO 90/09769 | 9/1990 |
| WO | 9403584 | 2/1994 |
| WO | WO 94/11008 | 5/1994 |
| WO | WO 95/05083 | 2/1995 |
| WO | WO 95/22301 | 8/1995 |
| WO | WO 95/06439 | 9/1995 |
| WO | WO 95/32623 | 12/1995 |
| WO | WO96/24304 | 8/1996 |
| WO | WO 96/24661 | 8/1996 |
| WO | WO 97/05193 | 2/1997 |
| WO | WO 97/37613 | 10/1997 |
| WO | WO 98/06445 | 2/1998 |
| WO | 9822154 | 5/1998 |
| WO | WO 98/22158 A2 | 5/1998 |
| WO | WO 98/22158 A3 | 5/1998 |
| WO | WO 98/30167 | 7/1998 |
| WO | WO 98/34569 | 8/1998 |
| WO | WO 98/40111 | 9/1998 |
| WO | WO 99/03979 | 1/1999 |
| WO | 9919005 | 4/1999 |
| WO | WO 99/43786 | 9/1999 |
| WO | WO 99/47188 | 9/1999 |
| WO | WO 00/15765 | 3/2000 |
| WO | WO 00/16822 | 3/2000 |
| WO | WO 00/24437 A2 | 5/2000 |
| WO | WO 00/24437 A3 | 5/2000 |
| WO | WO 00/32250 | 6/2000 |
| WO | WO 00/48550 | 8/2000 |
| WO | WO 00/72782 | 12/2000 |
| WO | WO 01/19423 | 3/2001 |
| WO | WO 01/39694 A2 | 6/2001 |
| WO | WO 01/39694 A3 | 6/2001 |
| WO | WO 01/45765 | 6/2001 |
| WO | WO 01/66159 | 9/2001 |
| WO | WO 01/70293 A1 | 9/2001 |
| WO | WO 02/22184 | 3/2002 |
| WO | WO 03/007784 | 1/2003 |
| WO | WO 03/007788 A2 | 1/2003 |
| WO | WO 03/007790 A2 | 1/2003 |
| WO | WO 03/097694 A1 | 11/2003 |

OTHER PUBLICATIONS

Resin Technology Group, LLC. "Viscosity chart," http://www.resintechgroup.com/tables/viscosity.html, accessed online Mar. 29, 2006. 1 page.*

Heywood, NI, et al. "Solids, Wet, Handling Problems" in McKetta, J.J., ed., Encyclopedia of Chemical Processing and Design, vol. 52 (1995, Marcel Dekker, New York). pp. 449-450.*

Hiles et al., "Mechanical properties of xenogeneic small-intestinal submucosa when used as an aortic graft in the dog", Journal of Biomedical Materials Research, vol. 29, 883-891, (1995).

Sandusky, et al., "Healing Comparison of Small Intestine Submucosa and ePTFE Grafts in the Canine Carotid Artery", J. Surg.Res., 58:415-420, (1995).

Knapp, et al., "Biocompatibility of Small-Intestine Submucosa in Urinary Tract as Augmentation Cystoplasty Graft and Injectable Suspension", J Endourology, 8:125-130, (1994).

Kropp et al., "Regenerative Bladder Augmentation: A Review of the Initial Preclinical Studies with Porcine Small Intestinal Submucosa", Muscle, Matrix, and Bladder Function, Plenum Press, New York, (1995).

Kropp et al., "Experimental Assessment of Small Intestinal Submucosa as a Bladder Wall Substitute", Urology 446:396-400, (1995).

Vaught et al., "Detrusor Regeneration in the Rat Using Porcine Small Intestinal Submucosa Grafts: Functional Innervation and Receptor Expression", J. Urol., 155:374-378, (1996).

Kropp et al, Characterization of Small Intestinal Submucosa Regenerated Canine Detrusor: Assessment of Reinnervation, In Vitro Compliance and contractility, J. of Urol., 156:599-607, (1996).

Kropp et al., "Regenerative Urinary Bladder Augmentation Using Small Intestinal Submucosa: Urodynamic and Histopatholoaic Assessment in Long-Term Canine Bladder Augmentations", Journal of Urology, 155:2098-2104, (1996).

Aiken et al., "Small Intestinal Submucosa as an Intra-Articular Ligamentous Graft Material: A Pilot Study in Dogs", Vet Comp Orthocedics Traumatology, 7:124-128, (1994).

Badylak et al., "The Use of Xenogeneic Small Intestinal Submucosa as a Biomaterial for Achille's Tendon Repair in a dog model", J Biomed Materials, 29:977-985, (1995).

Hodde et al., "The Effect of Range of Motion Upon Remodeling of Small Intestinal Submucosa (SIS) when used as an Achilles Tendon Repair Material in the Rabbit", *Tissue Engineering* 3, 1:27-37, (1997).

Ferrand et al., "Directional Porosity of Porcine Small-Intestinal Submucosa", *J Biomed Materials Res*, 27:1235-1241, (1993).

Hiles et al., "Porosity of Porcine Small-Intestinal Submucosa for use as a Vascular Graft", *J Biomed Materials Res*, 27: 139-144 (1993).

Hodde et al., "Glycosaminoglycan Content of Small Intestinal Submucosa: A Bioscaffold for Tissue Replacement", *Tissue Engineering*, 2:3 209-217, (1996).

Prevel et al., "Small Intestinal Submucosa: Utilization for Repair of Rodent Abdominal Wall Defects", *Ann Plast Surg*, 35:374-380, (1995).

Clarke et al., "Intestine Submucosa and Polypropylene Mesh for Abdominal Wall Repair in Dogs", *J Surg Res*, 60:107-114, (1996).

Prevel et al., "Small Intestinal Submucosa: Utilization as a Wound Dressing in Full-Thickness Rodent Wounds", *Ann Plast Surg*.,35:381-388, (1995).

Cobb et al., "Histology after Dural Grafting with Small Intestinal Submucosa", *Surgical Neurology*, 46: 389-394, (1996).

Cobb et al., "Porcine Small Intestinal Submucosa as a Dural Substitute", *Surgical Neurology*, 51:99-104, (1999).

Voytik-Harbin et al., "Application and Evaluation of the AlamarBlue Assay for Cell Growth and Survival of Fibroblasts", *Journal of Immunological Methods, In Vitro Cell Bio-Animal*, 34: 2399-246, (1998).

Suckow, M.A., "Enhanced Bone Regeneration Using Porcine Small Intestinal Submucosa", *J. Invest Surg*, 12: 277, (1999).

Badylak , S., et al., "Naturally Occurring Extracellular Matrix as a Scaffold for Musculoskeletal Repair", *Clin Orthop*, 3675:S333-S3433, (1999).

Cook, J.L. et al., "Induction of Meniscal Regeneration in Dogs Using a Novel Biomaterial", *Am J Sports Med*, 27: 658, (1999).

Dejardin, L.M. et al., "Use of small intestinal submucosal implants for regeneration of large fascial defects: an experimental study in dogs", J Biomed Mater Res, 46:203-211, (1999).

Sacks, M.S., et al., "Quantification of the fiber architecture and biaxial mechanical behavior of porcine intestinal submucosa", *J Biomed Mater Res*, 46:1-10, (1999).

COOK® News Releases, "COOK® Introduces Innovative Surgisis™ Soft Tissue Repair Biomaterial", (May 21, 2000).

COOK® News Releases, "COOK® Oasis™ Wound Dressing Biomaterial From COOK® Remodels Partial Thickness Skin Injuries", (Dec. 23, 1999).

COOK® News Releases, "Cook Incorporated Forms Dedicated Tissue Engineered Products Group", (Feb. 16, 2000).

COOK® News Releases, "FDA Clears Oasis™ Wound Dressing Biomaterial From COOK® for Full-Thickness Skin Injuries", (Jan. 24, 2000).

Klootwyk, et al., "The Use of Xenographic SIS as a Biomaterial for Achilles Tendon Repair in Dogs," First SIS Symposium, Dec. 1996, USA.

Lenz, et al., "SIS as an ACL Replacement in Dogs and Goats," First Symposium, Dec. 1996, USA.

Cook, et al., "Comparison of SIS Cancellous Bone as Substrates for Three-Dimensional Culture of Canine Articular Chondrocytes," First SIS Symposium, Dec. 1996, USA.

Badylak, et al., "Different Configurations of Small Intestinal Submucosa as a Biomaterial for Achilles Tendon Repair in a Dog Model," First SIS Symposium, Dec. 1996, USA.

Voytik-Harbin & Badylak, "Induction of Osteogenic Activity by Small Intestinal Submucosa in Rat Calvaria Non-union Defects," First SIS Symposium. Dec. 1996, USA.

Kandel, et al., "SIS and Reconstituted Cartilage and Its Use in Joint Resurfacing of Focal Defects in Rabbits," First SIS Symposium, Dec. 1996, USA.

Tullius, et al., "Differential Permeabilty of SIS," First SIS Symposium, Dec. 1996, USA.

Obermiller, et al., "Suture Retention Strength of SIS," First SIS Symposium, Dec. 1996, USA.

Shelton, et al., "Repair of the Canine Medial Meniscus using SIS: A Feasibility Study," Second SIS Symposium, Dec. 1998, USA.

Cook, et al., "Meniscal Regeneration in dogs Using Grafts of SIS," Second SIS Symposium, Dec. 1998, USA.

Welch, et al., "Healing of Canine Meniscal Defect with Small Intestinal Submucosa Implants," Dec. 1998, USA.

Solchaga, et al., "SIS as Delivery Vehicle for Mesenchymal Progenitor Cells," Dec. 1998, USA.

Paulino, et al., "The Use of an SIS-PGA Composite Graft for Repair of Cartilage Defect," Dec. 1998, USA.

Toombs and May, "Clinical Follow-Up of Three Canine ACL Reconstructions Using an SIS ACL Device," Dec. 1998, USA.

Tomasek and Gifford, "Small Intestinal Submucosa Matrix Regulates the Differentiation of Myofibroblasts," Third SIS Symposium, Nov. 2000, USA.

Cook, et al., "Tissue Engineering for Meniscal Repair Using SIS," Third SIS Symposium, Nov. 2000, USA.

Lifrak, et al., "Enhanced Repair of Goat Meniscal Defects Using Porcine Small Intestinal Submucosa (SIS)," Third SIS Symposium, Nov. 2000, USA.

Hoffman, "SIS Disc Replacement for the Temporomandibular Joint," Third SIS Symposium, Nov. 2000, USA.

Kaeding, "Use of SIS in the Surgical Treatment of Chronic Symptomatic Patella Tendinosis," Third SIS Symposium, Nov. 2000, USA.

Tomczak and Kaeding, "Use of SIS in the Surgical Treatment of Tendinosis About the Foot and Ankle," Third SIS Symposium, Nov. 2000, USA.

Moore, et al., "Bridging Segmental Defects in Long Bones With Intramedullary Tubes and Periosteal Sleeves Made From Small Intestinal Submucosa (SIS)," Third SIS Symposium, Nov. 2000, USA.

Wang, et al., "Small Intestinal Submucosa Enhances Healing of Medical Collateral Ligament in a Rabbit Model," Third SIS Symposium, Nov. 2000, USA.

Ojha, et al., "PGA-Plla Versus Small Intestinal Submucosa (SIS): A Comparison of Neo-Cartilage Grown From Two Scaffold Materials," Third SIS Symposium, Nov. 2000, USA.

Wiklerson, "Use of the Porcine Small Intestine Submucosal Tissue Graft and Repair of Rotator Cuff Tears," Third SIS Symposium, Nov. 2000, USA.

"Small Intestinal Submucosa," Third SIS Symposium, Nov. 2000, USA.

"Current Clinical Applications of SIS," Third SIS Symposium, Nov. 2000, USA.

Hodde, et al., "Glycosaminoglycan Content of Small Intestinal Submucosa: A Potential for GAG-Growth Interactions in SIS-Mediated Healing", First Symposium, Dec. 1996, USA.

Friess, "Collagen in drug delivery and tissue engineering", *Advanced Drug Delivery Reviews*, vol. 55, No. 12, 2003, pp. 1529-1530.

Olsen et al., "Recombinant collagen and gelatin for drug delivery", *Advanced Drug Delivery Reviews*, vol. 55, No. 12, 2003, pp. 1547-1557.

Aigner et al., "Collagens—major component of the physiological cartilage matrix, major target of cartilage degeneration, major tool in cartilage repair", *Advanced Drug Delivery Reviews*, vol. 55, No. 12, 2003, pp. 1569-1593.

Gelger et al., "Collagen sponges for bone regeneration with rhBMP-2", *Advanced Drug Delivery Reviews*, vol. 55. No. 12, 2003, pp. 1613-1629.

Ruszczak et al., "Collagen as a carrier for on-site delivery of antibacterial drugs", *Advanced Drug Delivery Reviews*, vol. 55, No. 12, 2003, pp. 1679-1698.

O'Grady et al., "Global regulatory registration requirements for collagen-based combination products: points to consider", *Advanced Drug Delivery Reviews*, vol. 55, No. 12, 2003, pp. 1699-1721.

Matthews et al., "Electrospinning of Collagen Type II: A Feasibility Study", *Journal of Bioactive and Compatible Polymers*, vol. 18, Mar. 2003, pp. 125-134.

Biscarini et al., "Growth of High Vacuum Sublimed Oligomer Thin Films", *ACS Polymer Preprints*, vol. 37, No. 2, 1998, pp. 618-619.

Biscarini et al., "Morphology and roughness of high-vacuum sublimed oligomer thin films", *Thin Solid Films*, vol. 439-443, 1996, pp. 284-285.

Biscarini et al., "Scaling Behavior of Anisotropic Organic Thin Films Grown in High-Vacuum", *Physical Review Letters*, vol. 78, No. 12, Mar. 24, 1997, pp. 2389-2392.

Voytik-Harbin et al., "Identification of Extractable Growth Factors from Small Intestinal Submucosa", *Journal of Cellular Biochemistry*, vol. 67, 1997, pp. 478-491.

McPherson, Ph.D. et al., "Characterization of Fibronectin Derived from Porcine Small Intestinal Submucosa", *Tissue Engineering*, vol. 4, No. 1, 1998, pp. 75-83.

Hodde, et al., "Vascular Endothelial Growth Factor in Porcine-Derived Extracellular Matrix", *Endothelium*, vol. 8(1), 2001, pp. 11-24.

Hodde et al., "Wounds: A Compendium of Clinical Research and Practice", Website: http:www.hmpcommunications.com/WNDS, Printed: Jul. 12, 2005, 7 pgs.

Hurst et al., "Mapping of the distribution of significant proteins and proteoglycans in small intestinal submucosa by fluorescence microscopy", *J. Biomater. Sci. Polymer Edn.*, vol. 12. No. 11, 2001, pp. 1267-1279.

Hodde et al., "Fibronectin peptides mediate HMEC adhesion to porcine-derived extracellular matrix", *Biomaterials*, vol. 23, 2002, pp. 1841-1848.

Hodde, "Naturally Occurring Scaffolds for Soft Tissue Repair and Regeneration", *Tissue Engineering*, vol. 8, No. 2, 2002, pp. 295-308.

Allman et al., Xenogeneic Extracellular Matrix Grafts Elicit a Th2-Restricted Immune Response, *Transplantation*, vol. 71, No. 11, Jun. 16, 2001, pp. 1631-1640.

Almon et al., "The Th2-Restricted Immune Response to Xenogeneic Small Intestinal Submucosa Does Not Influence Systemic Protective Immunity to Viral and Bacterial Pathogens", *Tissue Engineering*, vol. 8, No. 1, 2002, pp. 53-62.

Krëma, "Nonwoven Textiles", *Textile Trade Press*, Manchester, England, 1962, 6 pgs.

Answers.com, Definition of "freeze-dry", Accessed on May 12, 2005, 6 pgs.

Ma et al., "Microtubular architecture of biodegradable polymer scaffolds", *J. Biomed. Materials Res.*, vol. 56, No. 4, 2001, pp. 469-477.

Ma et al., "Biodegradable Polymer Scaffolds with Well-Defined Interconnected Spherical Pore Network", *Tissue Engineering*, vol. 7, No. 1, 2001, pp. 23-33.

Klawitter et al., "An Evaluation of Bone Growth Into Porous High Density Polyethylene", *J. Biomed. Materials Res.*, vol. 10, (1976) pp. 311-323.

White et al., "Biomaterial Aspects of Interpore-200 Porous Hydroxyapatite", *Dental Clinics of North America*, Reconstructive Implant Surgery and Implant Prosthodontics 1, vol. 30, No. 1, pp. 49-67.

Shors, Coralline Bone Graft Substitutes, *Orthopaedic Clinics of North America*, Bone Grafting and Bone Graft Substitutes, vol. 30, No. 4, Oct. 1999, pp. 599-613.

Wang, Experimental Study of Osteogenic Activity of Sintered Hydroxyapatite—On the Relationship of Sintering Temperature and Pore Size—, *J. Jpn. Orthop. Assoc.*, vol. 64, 1990, pp. 847-859.

Nehrer et al., "Matrix collagen type and pore size influence behavior of seeded canine chondrocytes", *Biomaterials*, vol. 18, No. 11, 1997, pp. 769-776.

Salem et al., "Interactions of 3T3 fibroblasts and endothelial with defined pore ffeatures", *J. Biomed Materials Res.*, vol. 61, No. 2, 2002, pp. 212-217.

P. K. Chu et al., "Plasma-surface modification of biomaterials", Materials Science and Engineering, Reports: A Review Journal, vol. 36, No. 5-6, Mar. 29, 2002, pp. 143-206.

Arnoczky et al., The microvasculature of the meniscus and its response to injury—An experimental study in the dog, *Am. J. Sports Med.*, 1983, 11(3); pp. 131-141.

Fox et al., Trephination of incomplete meniscal tears, *Arthroscopy*, 1993, 9(4); pp. 451-455.

Arnoczky et al., Meniscal repair using an exogenous fibrin clot—An experimental study of dogs, *J. Bone Joint Surg. Am.*, 1988, 70(8), pp. 1209-1216.

Rodeo, "Arthroscopic meniscal repair with use of the outside-in technique", *Instr. Course Lect.*, 2000, 49, pp. 195-206.

Stollsteimer et al., "Meniscal allograft transplantation: a 1- to 5-year follow-up of 22 patients", *Arhroscopy*, 2000, 16(4), pp. 343-347.

Rodeo, "Meniscal allografts—where do we stand?", *Am. J. Sports Med.*, 2001, 29(2), pp. 246-281.

Sweigart et al., "Toward tissue engineering of the knee meniscus", *Tissue Eng.*, 2001, 7(2), pp. 111-129.

Boss et al., "Technical innovative: creation of a peripheral vascularized trough to enhance healing in cryopreserved meniscal allograft reconstruction", *Knee Surg Sports Traumatol Arthrosc.*, 2000, 8(3), pp. 159-162.

Siegel et al., "Meniscal allografts", *Clin Sports Med.*, 1993, 12(1), pp. 59-80.

Klompmaker et al., "Meniscal replacement using a porous polymer prosthesis: a preliminary study in the dog.", *Biomaterials*, 1996, 17(12), pp. 1169-1175.

de Groot et al., "Use of porous polyurethanes for meniscal reconstruction and meniscal protheses", *Biomaterials*, 1996, 17(2), pp. 183-173.

Spaans et al., "Solvent-free fabrication of micro-porous polyurethane amide and polyurethane-urea scaffolds for repair and replacement of the knee-joint meniscus", *Biomaterials*, 2000, 21(23), pp. 2453-2460.

Stone et al., "Regeneration of meniscal cartilage with use of a collagen scaffold—Analysis of Preliminary data", *J. Bone Joint Surg. Am.*, 1997, 79(12), pp. 1770-1777.

Rodkey et al., "A clinical study of collagen meniscus implants to restore the injured meniscus", *Clin. Orthop.*, 1999, 49(387 Suppl.), pp. S281-S292.

Definitions from Onelook.com for "trimethyten" and "trimethylene".

J.S. Pieper et al "Preparation and characterization of porous crosslinked collagenous matrices containing bioavailable chondroitin suplhate" Biomaterials 1999, 20: 847-858.

P.B. van Wachem et al. "In vivo biocompatability of carbodiimide-crosslinked collagen matrices: Effects of crosslink density, heparin immobilization, and bFGF loading" J. Biomed. Mater. Res. 2001, 55 (3):368-378.

Kyumin Whang "A biodegradable polymer scaffold for delivery of osteotropic factors" Biomaterials 2000, 21 (24): 2545-2551.

J.S. Pieper et al. Attachment of glycosaminoglycans to collangenous matrices modulates the tissue response in rats, Biomaterials 2000, 21 (16): 1689-1699.

Kristen Billiar et al. "Effects of carbodiimide crosslinking conditions on the physical properties of laminated intestinal submucosa", J. Biomed. Mater. Res. 2001, 51(1): 101-108.

Toshimitsu Momose et al. "Surface modification of extrasynovial tendon by chemically modified hyaluronic acid coating" J. Biomed. Mater. Res. 2002, 59: 219-224.

Handbook of Biodegradable Polymers Hardwood Press 1997 (251-272).

Cohn et al., "Biodegradable PEO/PLA block copolymers," Journal of Biomedical Materials Research, 1988, 22 (993-1009).

"Polymer Preprints" (ACS Division of Polymer Chemistry), 1989. 30 (1): 498.

The Encyclopedia of Polymer Science, 1988 (13) 31-41.

"Handbook of Biodegradable Polymers" Hardwood Press 1997 (161-182).

"Handbook of Biodegradable Polymers" Hardwood Press 1997 (99-118).

DiSilvestro et al., "Effects of Cross-Linking on the Mechanical Properties of a Porous Foam Scaffold of Small Intestine Submucosa", Society for Biomaterials 29th Annual Meeting Transactions, 2003, pp. 88.

Ide et al., "Collagen Hybridization with Poly(l-Lactic Acid) Braid Promotes Ligament Cell Migration", Mater. Sci. Eng. C, 17(1-2), 95-99 (2001).

Bercovy et al., "Carbon-PGLA Prosthesis for Ligament Reconstruction Experimental Basis and Short Term Results in Man", Clin. Orthop. Relat. Res., (196), 159-68 (1985).

Zhu et al, "Immobilization of Biomacromolecules onto Aminolyzed Poly(L-lactic acid) toward Acceleration of Endothelium Regeneration", Tissue Engineering, v 10, pp. 53-61, 2004.

Cheng & Teoh, "Surface modification of ultra thin poly (ÿ caprolactone) films using acrylic acid and collagen", Biomaterials, v25(11), pp. 1991-2001, 2004.

Wan et al., "Cell adhesion on gaseous plasma modified poly-(L-lactide) surface under shear stress field", Biomaterials, v24(21), pp. 3757-3764, 2003.

Yang et al., "Effect of surface treatment on the biocompatibility of microbial polyhydroxyalkanoates", Biomaterials, v 23 (5), pp. 1391-1397, 2002.

Croll et al., "Controllable surface modification of Poly(lactic-co-glycolic acid) (PLGA) by hydrolysis or aminolysis I: physical, chemical, and theoretical aspects", Biomacromolecules, Mar.-Apr. 2004, 5(2): 463-473.

Kwon et al., "Fibroblast culture on surface-modified poly (glycolide-co-ÿ-caprolactone) scaffold for soft tissue regeneration", J. Biomater Sci Polym ed. 2001, 12(10) 1147-60.

Gastel JA, Muirhead WR, Lifrak JT, Fadale PD, Hulstyn MJ, Labrador DP "Meniscal tissue regeneration using a collagenous biomaterial derived from porcine small intestine submucosa", Arthroscopy, February; 17(2): 151-159.

Tan W, Krishnaraj R, Desai TA "Evaluation of nanostructured composite collagen-chitosan matrices for tissue engineering", Tissue Eng Apr; 7(2): 203-210, 2001.

Arnoczky SP "Building a meniscus", Biological considerations, Clin Orthop Oct; 367 (suppl), S244-53, 1999.

Metcalf et al., "Surgical technique for xenograft (SIS) augmentation of rotator-cuff repairs", Op Tech Orthop, 12(3): 204-208, 2002.

Courtney et al., "Modification of polymer surfaces: optimization of approaches", Perfusion, v 18 (11), pp. 33-39, 2003.

Zhang et al., Design of nanostructured biological materials through self-assembly of peptides and proteins, MIT Current Opinion in chemical Biology, 2002, 6:865-871.

Hodde and Hiles, "Bioactive FGF-2 in sterilized extracellular matrix", Wounds, 13(5): 195-201 (2001).

O'Meara, Patrick, "The basic science of meniscus repair," Orthopaedic review, Jun. 1993, pp. 681-686.

Supplementary European Search Report, Appln No. 02753403.1 (PCT/US 223190) dated Dec. 21, 2006 (3 pages).

Definitions of "intertwine" and "twine." American Heritage Dictionary of the English Language Online. Accessed Sep. 29, 2005. 2 pages.

On-line Medical Dictionary definition of "extracellular matrix" located at http://cancerweb.ncl.ac.uk/cgibin/omd?extracellular+matrix.

European Search Report for European Patent Application No. 02752339.8-1219, Mar. 19, 2007, 5 pgs.

European Examination Report for European Patent Application No. 02752339.8-1219, Jul. 20, 2007, 5 pgs.

"Urschel Laboratories, Inc.—Comitrol Processor Model 1700", http://www.urschel.com/Comitrol_Processor_Model_1700_df.html. Printed Jul. 9, 2008, 2 pgs.

Clearfix screw advertisement, 1998, Innovasive devices, Inc.

Winters and Justin, "Clearfix meniscal screw", Innovasive devices, Inc. 1998.

Surgical dynamics, meniscal stapler advertisement, 1997.

Bionix implants, Meniscus arrow advertisement, 1996.

Instrument makar, inc., Meniscus mender II, 1989.

William G. Clancy, Jr., M.D., and Ben K. Graf, M.D., "Arthroscopic Meniscal Repair," ACUFEX Microsurigal Inc., advertisement, 1988.

Wikipedia online definition of "hyaluronic acid" at http://en.wikipedia.org/wiki/Hyaluronate, Jul. 6, 2006.

Michael W. King, Ph.D., online article entitled "Extracellular Matrix (ECM)", at http://web.indstate.edu/thcme/mwking/extracellular_matrix.html, Jul. 6, 2006.

Owen, et al., "Calcification Potential of Small Intestinal Submucosa in a Rat Subcutaneous Model", Journal of Surgical Research, vol. 71, pp. 179-186, 1997.

Dix et al., "Myosin mRNA Accumulation and Myofibrillogenesis at the Myotendinous Junction of Stretched Muscle Fibers", The Journal of Cell Biology, vol. 111, Nov. 1990, pp. 1885-1894.

De Deyne, Ph.D., MPT et al., "The Adaptation of Perimuscular Connective Tissue During Distraction Osteogenesis", Clinical Orthopaedics and Related Research, No. 379, pp. 259-269.

Kannus et al., "The effect of immobilization on myotendinous junction: an ultrastructural, histochemical and immunohistochemical study", Acta Physical Scandinavica, vol. 144, 1992, pp. 387-394.

Tidball, Ph.D. et al., "Myotendinous Junction Injury in Relation to Junction Structure and Molecular Composition", *Exercise & Sport Sciences Reviews*, vol. 19, 1991, pp. 419-445.

European Search Report for European Application No. 05257903.4-2115, Jun. 14, 2006, 3 pgs.

Fan, et al., "A composite coating by electrolysis-induced collagen self-assembly and calcium phosphate minteralization", Biomaterials, Elsevier Science Publishers BV, XP004670973, vol. 26, No. 14, May 14, 2005, pp. 1623-1632.

Marino et al., "The effect of electric current on rat tail tendon collagen in solution", Calcified Tissue Research, XP009066270, vol. 4, No. 4, 1970, pp. 330-338.

Marino et al., "Piezoelectricity in collagen films", Calcified Tissue International, XP009066271, vol. 31, No. 3, 1980, pp. 257-259.

Miller et al., Electric field-assisted assembly of type-I collagen for applications in biomedical micro-systems, Proceedings of IMECE 2005, 2005 ASME Int'l Mech. Engr. Cong. and Expo., XP009065904, Nov. 2005, pp. 1-3.

Niyibizi et al., "Human Placenta Type V Collagens Evidence for the Existence of an Alpha-1-V-Alpha-2-V-Alpha-3-V Collagen Molecule", Journal of Biological Chemistry, XP002380121, vol. 259, No. 22, 1984, pp. 14170-14174.

Ma et al., "Synthetic nano-scale fibrous extracellular matrix", Journal Biomedical Materials Research, XP002380122, vol. 46, No. 1, 1999, pp. 60-72.

European Search Report for European Application No. 05257908.3-2107, Aug. 9, 2006, 3 pgs.

Sarikaya et al., "Antimicrobial Activity Associated with Extracellular Matrices", Tissue Engineering, vol. 8, No. 1, 2002, pp. 63-71.

Definitions of "comminute" and "slurry", Dictionary.com; Accessed Sep. 20, 2005, 2 pgs.

* cited by examiner

POROUS EXTRACELLULAR MATRIX SCAFFOLD AND METHOD

This application claims priority under 35 U.S.C. §119(e) to U.S. Provisional Application No. 60/305,786, filed Jul. 16, 2001; and U.S. Provisional Application No. 60/388,761, filed Jun. 14, 2002, both of which are expressly incorporated by reference herein.

CROSS REFERENCE

Cross reference is made to U.S. patent applications Ser. No. 10/195.794 entitled "Meniscus Regeneration Device and Method"; Ser. No. 10/195,719 entitled "Devices from Naturally Occurring Biologically Derived Materials"; Ser. No. 10/195,347 entitled "Cartilage Repair Apparatus and Method"; Ser. No. 10/195,344 entitled "Unitary Surgical Device and Method"; Ser. No. 10/195,341 entitled "Hybrid Biologic/Synthetic Porous Extracellular Matrix Scaffolds"; Ser. No. 10/195,606 entitled "Cartilage Repair and Regeneration Device and Method"; Ser. No. 10/195,334 entitled "Cartilage Repair and Regeneration Scaffolds and Method"; and Ser. No. 10/195,633 entitled "Porous Delivery Scaffold and Method" each of which is assigned to the same assignee as the present application, each of which is filed concurrently herewith, and each of which is hereby incorporated by reference. Cross reference is also made to U.S. patent application Ser. No. 10/172,347 entitled "Hybrid Biologic-Synthetic Bioabsorbable Scaffolds" which was filed on Jun. 14, 2002, which is assigned to the same assignee as the present application, and which is hereby incorporated by reference.

FIELD OF THE DISCLOSURE

The present disclosure relates generally to an extracellular matrix scaffold, and more particularly to a porous extracellular matrix scaffold for repairing or regenerating body tissue and a method for making such a scaffold.

BACKGROUND

Naturally occurring extracellular matrices (ECMs) are used for tissue repair and regeneration. One such extracellular matrix is small intestine submucosa (SIS). SIS has been used to repair, support, and stabilize a wide variety of anatomical defects and traumatic injuries. Commercially-available SIS material is derived from porcine small intestinal submucosa that remodels to the qualities of its host when implanted in human soft tissues. Further, it is taught that the SIS material provides a natural matrix with a three-dimensional microstructure and biochemical composition that facilitates host cell proliferation and supports tissue remodeling. Indeed, SIS has been shown to contain biological molecules, such as growth factors and glycosaminoglycans that aid in the repair of soft tissue of the human body. The SIS material currently being used in the orthopaedic field is provided in a dried and layered configuration in the form of a patch to repair or regenerate soft tissue such as tendons, ligaments and rotator cuffs.

While small intestine submucosa is readily available, other sources of ECM are known to be effective for tissue remodeling. These sources include, but are not limited to, stomach, bladder, alimentary, respiratory, or genital submucosa, or liver basement membrane. See, e.g., U.S. Pat. Nos. 6,379,710, 6,171,344; 6,099,567; and 5,554,389, each of which is hereby incorporated by reference.

Further, while SIS is most often porcine derived, it is known that various submucosa materials may also be derived from non-porcine sources, including bovine and ovine sources. Additionally, the ECM material may also include partial layers of laminar muscularis mucosa, muscularis mucosa, lamina propria, stratum compactum and/or other such tissue materials depending upon factors such as the source from which the ECM material was derived and the delamination procedure.

As used herein, it is within the definition of a naturally occurring extracellular matrix to clean, delaminate, and/or comminute the extracellular matrix, or to cross-link the collagen or other components within the extracellular matrix. It is also within the definition of naturally occurring extracellular matrix to fully or partially remove one or more components or subcomponents of the naturally occurring matrix. However, it is not within the definition of a naturally occurring extracellular matrix to separate and purify the natural components or subcomponents and reform a matrix material from purified natural components or subcomponents. Thus, while reference is made to SIS, it is understood that other naturally occurring extracellular matrices (e.g. stomach, bladder, alimentary, respiratory, and genital submucosa, and liver basement membrane), whatever the source (e.g. bovine, porcine, ovine) are within the scope of this disclosure. Thus, in this application, the terms "naturally occurring extracellular matrix" or "naturally occurring ECM" are intended to refer to extracellular matrix material that has been cleaned, processed, sterilized, and optionally crosslinked. The following patents, hereby incorporated by reference, disclose the use of ECMs for the regeneration and repair of various tissues: U.S. Pat. Nos. 6,379,710; 6,187,039; 6,176,880; 6,126,686; 6,099,567; 6,096,347; 5,997,575; 5,993,844; 5,968,096; 5,955,110; 5,922,028; 5,885,619; 5,788,625; 5,762,966; 5,755,791; 5,753,267; 5,733,337; 5,711,969; 5,645,860; 5,641,518; 5,554,389; 5,516,533; 5,460,962; 5,445,833; 5,372,821; 5,352,463; 5,281,422; and 5,275,826.

The manipulation of scaffold pore size, porosity, and interconnectivity is an important science contributing to the field of tissue engineering (Ma and Zhang, 2001, J Biomed Mater Res, 56(4):469-477; Ma and Choi, 2001 Tissue Eng, 7(1):23-33) because it is believed that the consideration of scaffold pore size and density/porosity influences the behavior of cells and the quality of tissue regenerated. In fact, several researchers have shown that different pore sizes influence the behavior of cells in porous three-dimensional matrices. For example, it has been demonstrated in the art that for adequate bone regeneration to occur scaffold pore size needs to be at least 100 microns (Klawitter et al., 1976, J Biomed Mater Res, 10(2): 311-323). For pore sizes and interconnectivity less than that, poor quality bone is regenerated and if pore size is between 10-40 microns bone cells are able to form only soft fibrovascular tissue (White and Shors, 1991, Dent Clin North Am, 30:49-67). The consensus of research for bone regeneration indicates that the requisite pore size for bone regeneration is 100-600 microns (Shors, 1999, Orthop Clin North Am, 30(4): 599-613; Wang, 1990, Nippon Seikeigeka Gakki Zasshi, 64(9):847-859). It is generally known in the art that optimal bone regeneration occurs for pore sizes between 300-600 microns.

Similarly, for the regeneration of soft orthopaedic tissues, such as ligament, tendon, cartilage, and fibro-cartilage, scaffold pore size is believed to have a substantial effect. For example, basic research has shown that cartilage cells (chondrocytes) exhibit appropriate protein expression (type II collagen) in scaffolds with pore sizes of the order of 20 microns and tend to dedifferentiate to produce type I collagen in scaffolds with nominal porosity of about 80 microns (Nehrer et al., 1997, Biomaterials, 18(11):769-776). More recently, it has been shown that cells that form ligaments, tendons, and blood vessels (fibroblasts and endothelial cells) exhibit significantly different activity when cultured on scaffolds with differing pore sizes ranging from 5 to 90 microns (Salem et al., 2002, J Biomed Mater Res, 61(2):212-217).

SUMMARY

According to one illustrative embodiment, there is provided a method of making an implantable scaffold for repairing damaged or diseased tissue. The method includes the step of suspending, mixing, or otherwise placing pieces of a naturally occurring extracellular matrix material in a liquid. The naturally occurring extracellular matrix material and the liquid are formed into a mass. The liquid is subsequently driven off so as to form interstices in the mass. In one specific implementation of this exemplary embodiment, the liquid is driven off by freeze drying the naturally occurring extracellular matrix material and the liquid in which it is suspended. In such a manner, the liquid is sublimed thereby forming the interstices in the mass.

The material density and pore size of the scaffold may be varied by controlling the rate of freezing of the suspension. The amount of water into which the pieces of naturally occurring extracellular matrix material is suspended may also be varied to control the material density and pore size of the resultant scaffold.

In accordance with another exemplary embodiment, there is provided an implantable scaffold for repairing or regenerating tissue which is prepared by the process described above.

In another aspect, the present disclosure provides an implantable scaffold for repairing or regenerating body tissue. The scaffold comprises a porous body of naturally occurring extracellular matrix pieces that are interconnected to define an interior surface of the body. The interior surface has a three-dimensional topography of irregular shape.

In another aspect, the present disclosure provides an implantable device for repairing or regenerating body tissue. The device comprises a three-dimensional reticulated foam comprising a plurality of interconnected pores. The interconnected pores define three-dimensional interconnected passageways having irregular shapes. At least part of the reticulated foam comprises naturally occurring extracellular matrix.

In another aspect, the present disclosure provides a method of making an implantable device for repairing or regenerating body tissue. The method comprises the steps of providing a naturally occurring extracellular matrix material in a raw form, comminuting the raw naturally occurring extracellular matrix in the presence of a liquid to form a slurry of naturally occurring extracellular matrix, and lyophilizing the slurry of naturally occurring extracellular matrix to form a reticulated foam of naturally occurring extracellular matrix.

In another aspect, the present disclosure provides a method of making an implantable scaffold for repairing or regenerating body tissue. The method comprises the steps of providing a naturally occurring extracellular matrix material in a raw form, comminuting the raw naturally occurring extracellular matrix to form cohesive pieces of naturally occurring extracellular matrix, and lyophilizing the cohesive pieces of naturally occurring extracellular matrix to form a reticulated foam of naturally occurring extracellular matrix.

The implantable devices disclosed herein are three dimensional, porous scaffolds of ECMs like SIS. As such, it is evident that an implant based on the teachings of the present disclosure will have the dual advantage of having not only the appropriate biochemistry (collagens, growth factors, glycosaminoglycans, etc. naturally found in such ECMs) but also the appropriate physical microstructure to enable desired cellular activity upon implantation. These implantable devices are likely to find therapeutic use in the orthopaedic field, for devices used in the treatment of diseased or damaged fibro-cartilage such as the meniscus, diseased or damaged articular cartilage, and diseased or damaged bone.

The above and other features of the present disclosure will become apparent from the following description and the attached drawings.

BRIEF DESCRIPTION OF THE DRAWINGS

The detailed description particularly refers to the accompanying figures in which.

DETAILED DESCRIPTION OF THE DRAWINGS

Figure 1:
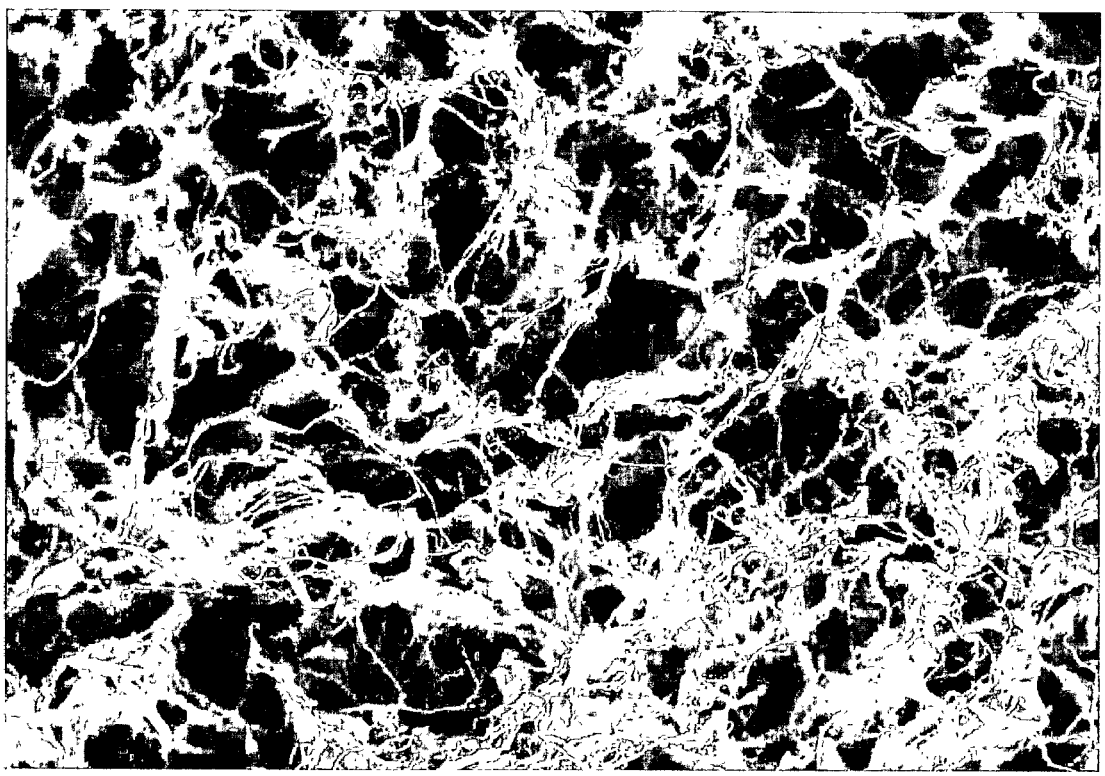
FIG. 1 is an image from a scanning electron microscope which shows the surface of a porous reticulated SIS open cell foam scaffold having a relatively large pore size and a relatively low material density.

The present disclosure relates to a porous scaffold for implanting into the body of a patient to repair or regenerate damaged or diseased tissue. The porous scaffold is constructed from a naturally occurring extracellular material. For example, the scaffold may be constructed from SIS. As will be discussed herein in greater detail, both the material density and the pore size of the porous scaffold may be varied to fit the needs of a given scaffold design.

Such porous scaffolds may be fabricated by suspending pieces of an extracellular matrix material in a liquid. As used herein, the term "piece" is intended to mean any fiber, strip, ribbon, sliver, filament, shred, bit, fragment, part, flake, slice, cut, chunk, or other portion of solid or solid-like material. Also, as used herein, the term "suspending" is intended to include any placement of a solid (e.g., pieces of ECM) in a liquid whether or not an actual suspension is created. As such, the term "suspending" is intended to include any mixing of a solid in a liquid or any other placement of a solid in a liquid. As a result, the term "suspension" is likewise not intended to be limited to suspensions, but rather is intended to mean any mass having a solid present in a liquid.

In any event, the suspension of the pieces of extracellular matrix material and the liquid forms a mass in the form of, for example, a "slurry". The liquid may then be subsequently driven off of the mass so as to form interstices therein. The liquid may be driven off in a number of different manners. For example, as will herein be described in greater detail, the liquid may be driven off via sublimation in a freeze drying process. Alternatively, the liquid may also be driven off by subjecting the suspension to either an unheated vacuum process or a vacuum under a controlled heating process. The liquid may also be driven off from the suspension ultrasonically. Microwave energy, RF energy, UV energy, or any other type of energy (or combination thereof) may also be utilized to drive the liquid off of the suspension. Liquid may also be driven off of the suspension by forcing or drawing air through the suspension. The suspension may be centrifuged to drive off the liquid. Moreover, the liquid may include a water-soluble filler which is driven off, for example, by use of an alcohol. In short, the present disclosure contemplates the driving off of the liquid from the suspension by any liquid removal process.

As alluded to above, while any of the aforementioned processes for driving off the liquid from the suspension may be utilized, along with any other process known by one skilled in the art, the processes of the present disclosure will herein be exemplary described in regard to a lyophilization process (i.e., freeze drying). However, it should be understood that such a description is merely exemplary in nature and that any one or more of the aforedescribed processes for driving off the liquid from the suspension may be utilized to fit the needs of a given scaffold design or process design.

As alluded to above, one useful process for fabricating the porous scaffolds of the present disclosure is by lyophilization. In this case, pieces of an extracellular matrix material are suspended in a liquid. The suspension is then frozen and subsequently lyophilized. Freezing the suspension causes the liquid to be turned to ice crystals. These ice crystals are then sublimed under vacuum during the lyophilization process thereby leaving interstices in the material in the spaces previously occupied by the ice crystals. The material density and pore size of the resultant scaffold may be varied by controlling, amongst other things, the rate of freezing of the suspension and/or the amount of water in which the extracellular matrix material is suspended in at the on-set of the freezing process.

As a specific example of this process, fabrication of a porous SIS scaffold by lyophilization will be described in detail. However, it should be appreciated that although the example is herein described in regard to an SIS scaffold, fabrication of a scaffold constructed from other extracellular matrix materials may also be performed in a similar manner.

The first step in fabricating a porous scaffold with a desired pore size and density is the procurement of comminuted SIS. Illustratively, scissor-cut SIS runners (~6" long) are positioned in a 1700 series Comitrol™ machine, commercially available from Urschel Laboratories (Valparaiso, Ind.). The SIS material is processed in the presence of a liquid and thereafter collected in a receptacle at the output of the machine. The material is then processed through the machine a second time under similar conditions. In one exemplary process, a liquid (e.g., water) is introduced into the input of the machine contemporaneously with the SIS material. The resultant material is a "slurry" of SIS material (thin, long SIS fibers ~200 microns thick×1-5 mm long) suspended in a substantially uniform manner in water. Although the suspension is herein described as being formed as a byproduct of the comminuting process, it should be appreciated that the pieces of SIS may be suspended in the liquid (i.e., water) in other manners known to those skilled in the art. Furthermore, while other methods are known for comminuting SIS, it is understood that for the purposes of the present disclosure, comminuted SIS comprises, ribbon-like or string-like fibers wherein at least some of the individual pieces of ECM and SIS material have lengths greater than their widths and thicknesses. Such fibers may be interlaced to provide a felt-like material, if desired.

Process parameters can be varied using the above-identified 1700 series Comitrol™ machine, including the choice of blade used, whether water is used, the amount of water used, the speed at which the blades turn, and the number of times the material is passed through the machine. As an example, cutting head 140084-10 and a Vericut, sealed impeller from Urschel Laboratories may be used, with a flow of water of about two (2) gallons per minute, with the blade running at a constant speed of about 9300 rpm. A first pass through the machine at these parameters will produce fibrous SIS material of varying sizes, and a second pass will produce SIS fibers of a more uniform size. By way of example, the comminuted material may be tested to determine if it has the consistency of that which is desired for use in regard to the illustrative embodiments described herein by the following process: the comminuted SIS suspension or slurry is centrifuged, excess water is poured off and the remaining slurry is poured into a dish. By hand, a small amount of the comminuted SIS material in the dish is pinched between the thumb and index finger and gently lifted from the dish. Illustratively, at least a small amount of additional SIS, beyond the portion pinched between the thumb and index finger, will lift along with the material that has been pinched ("pinch test"). This additional comminuted SIS material lifts with the material that is between the thumb and index finger because the individual pieces of comminuted SIS material are commingled or intertwined.

Figure 9:
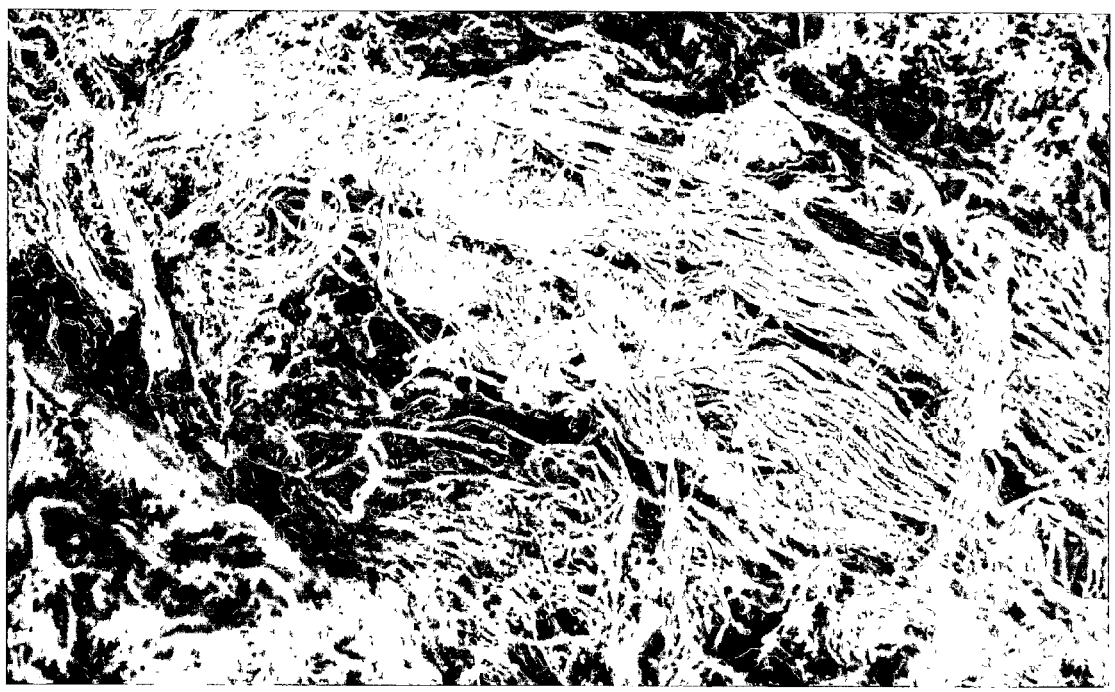
FIGS. 9 and 10 are images from a scanning electron microscope which show a mass of cohesive SIS pieces.
Figure 10:
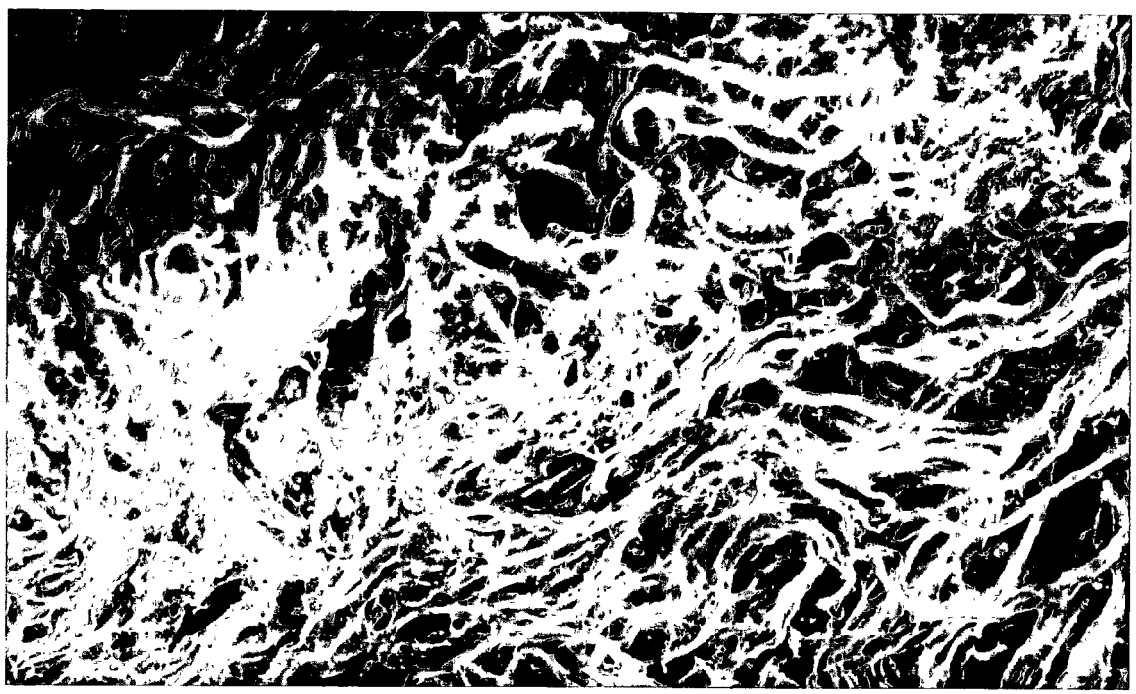

The terms "cohesive ECM", "cohesive SIS", "cohesive ECM pieces" and "cohesive SIS pieces" are used herein to respectively denote ECM or SIS material that has been comminuted or otherwise physically processed to produce ECM or SIS pieces that are capable of comingling or intertwining (in the wet or dry state) to form a mass of discrete pieces of ECM or SIS that remain massed together under some conditions (such as under gravity), regardless of the shape or shapes of the individual ECM or SIS pieces. One method of demonstrating that the ECM or SIS material comprises cohesive pieces is the "pinch test" described in the preceding paragraph. Examination of the final ECM or SIS product produced may also provide evidence that the base material comprised cohesive ECM or SIS pieces. Illustratively, the ECM or SIS pieces are sufficiently cohesive to each other (or to other pieces in the mix or slurry) that they remain unified throughout the process used to produce the foam structure. Examples of cohesive SIS pieces are shown in the scanning electron microscopic images of FIGS. 9 and 10.

Thereafter, the comminuted SIS suspension is frozen and lyophilized (i.e., freeze dried). In particular, the SIS suspension is frozen at a controlled rate of temperature drop to control the size of the formed ice crystals. Once frozen, and without allowing the material to thaw, the lyophilization process sublimes the ice crystals directly to a vapor under vacuum and low temperatures. This leaves voids or interstices in the spaces previously occupied by the ice crystals.

Any commercially available freezer for freezing the suspension to a desired temperature may be used. Likewise, any commercially available lyophilizer may be used for the lyophilization process. One exemplary machine for performing the lyophilization process is a Virtis Genesis™ Series lyophilizer which is commercially available from SP Industries, Inc. of Gardiner, N.Y.

The process parameters of the aforedescribed fabrication process may be varied to produce scaffolds of varying pore sizes and material densities. For example, the rate at which the suspension is frozen, the amount of water present in the suspension, or the compactness of the extracellular matrix material may be varied to produce scaffolds of varying pore sizes and material densities.

For instance, to produce scaffolds having a relatively large pore size and a relatively low material density, the extracellular matrix suspension may be frozen at a slow, controlled rate (e.g., $-1°$ C./min or less) to a temperature of about $-20°$ C., followed by lyophilization of the resultant mass. To produce scaffolds having a relatively small pore size and a relatively high material density, the extracellular matrix material may be tightly compacted by centrifuging the material to remove a portion of the liquid (e.g., water) in a substantially uniform manner prior to freezing. Thereafter, the resultant mass of extracellular matrix material is flash-frozen using liquid nitrogen followed by lyophilization of the mass. To produce scaffolds having a moderate pore size and a moderate material density, the extracellular matrix material is first tightly compacted by centrifuging the material to remove a portion of the liquid (e.g., water) in a substantially uniform manner prior to freezing. Thereafter, the resultant mass of extracellular matrix material is frozen at a relatively fast rate (e.g., $>-1°$ C./min) to a temperature of about $-80°$ C. followed by lyophilization of the mass.

EXAMPLE 1

Example 1 demonstrates the fabrication of a porous SIS scaffold having a relatively large pore size and a relatively low material density. Such scaffolds are obtained by freezing a comminuted SIS suspension at a slow, controlled rate ($-1°$ C./min or less) to $-20°$ C., followed by lyophilization. The procedure is as follows. First, comminuted SIS is fabricated as described above. Specifically, scissor-cut SIS runners (~6" long) are placed in a suitable comminuting machine such as the Urschel Comitrol machine described above. The comminuted SIS is collected in a receptacle at the output of the machine. The collected material is then processed through the machine a second time, under the same conditions as before. The resultant mass is a "slurry" of SIS material (thin, long SIS fibers ~200 microns thick×1-5 mm long) suspended relatively uniformly in water.

Next, a slow-freeze ethanol bath is prepared as follows. Pour enough ethanol to obtain about a 1 centimeter head in a flat-bottomed plastic container large enough to hold four 24-well culture plates. Place the container in a $-20°$ C. freezer. The mass of each of four empty twenty-four well plates is then recorded. Under a sterile hood using sterile conditions, an approximately 3 ml aliquot of the comminuted SIS material is placed in each well of the tissue culture plates. The mass of each full plate of material is then recorded. The four culture plates are then placed into the ethanol freeze bath and allowed to freeze overnight.

The frozen plates are then removed from the ethanol bath and placed in a suitable lyophilization machine such as the Virtis Genesis Series lyophilizer described above. Without allowing the frozen SIS material to thaw, the process of lyophilization sublimes ice crystals directly to vapor under vacuum and low temperatures. This leaves voids or interstices in the spaces previously occupied by the ice crystals. In this case, the parameters used in the lyophilization process include a first period at a primary drying temperature of $-13°$ C. for 8 hours, followed by a second period at a secondary drying temperature of $35°$ C. for 4 hours.

After the lyophilization cycle is complete, the plates are removed from the lyophilization machine and the mass of each plate is determined and recorded. The results from this process are summarized in the following table:

| Average Volume | Average Mass | Average Density |
| --- | --- | --- |
| 1.249 ml | 0.007396 g | 0.006 (g/cc) |

A scanning electron image of the surface of the samples was taken to visualize the relative pore sizes. These pore sizes are about 600 microns to about 700 microns. An image indicative of the samples prepared in accordance with Example 1 is shown in FIG. 1.

Figure 2:
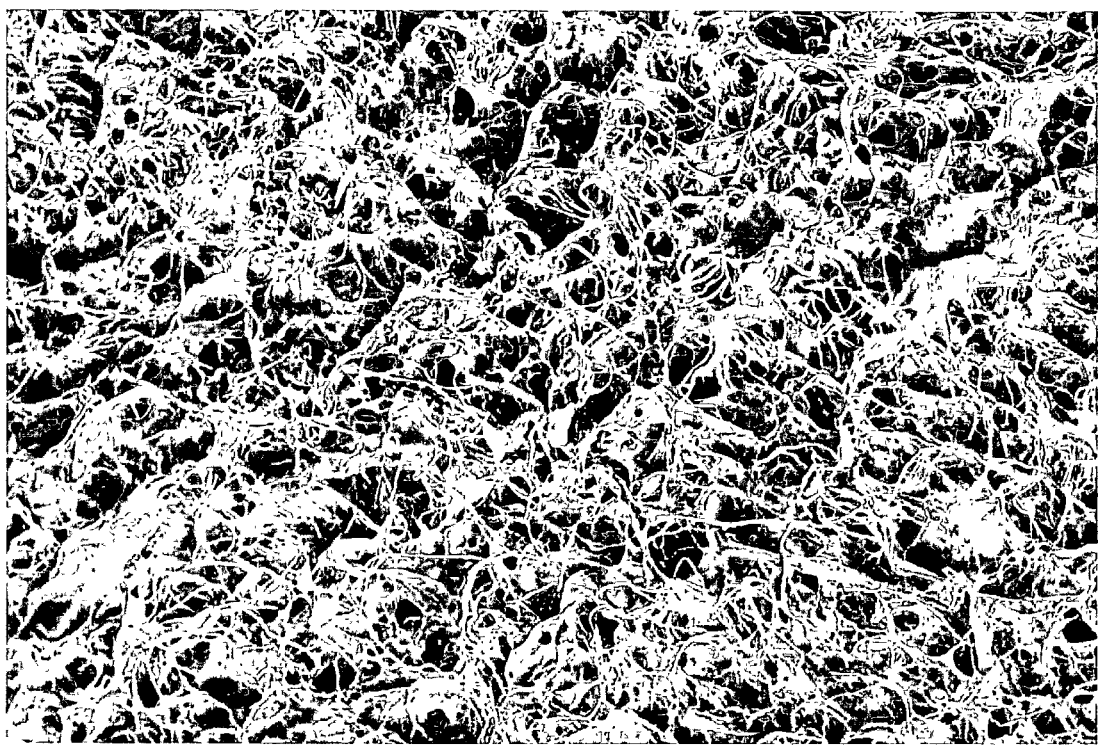
FIG. 2 is an image from a scanning electron microscope which shows the surface of a porous reticulated SIS open cell foam scaffold having a relatively moderate pore size and a relatively moderate material density.
Figure 3:
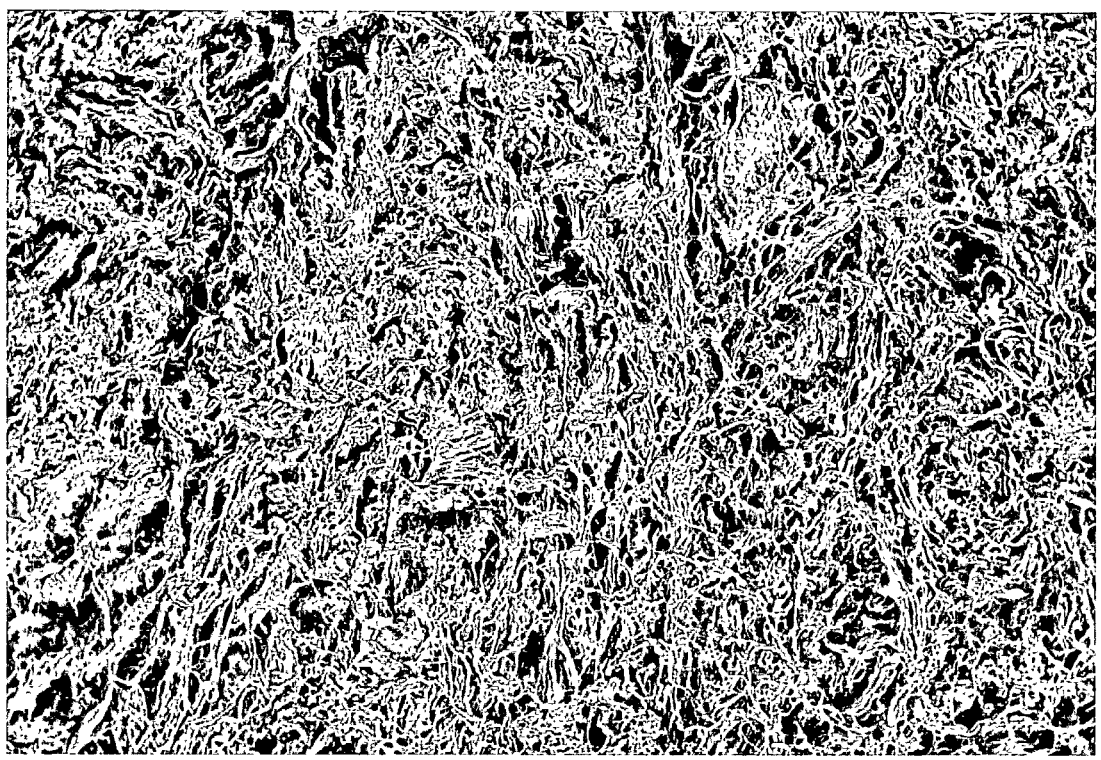
FIG. 3 is an image from a scanning electron microscope which shows the surface of a porous reticulated SIS open cell foam scaffold having a relatively small pore size and a relatively high material density.
Figure 4:
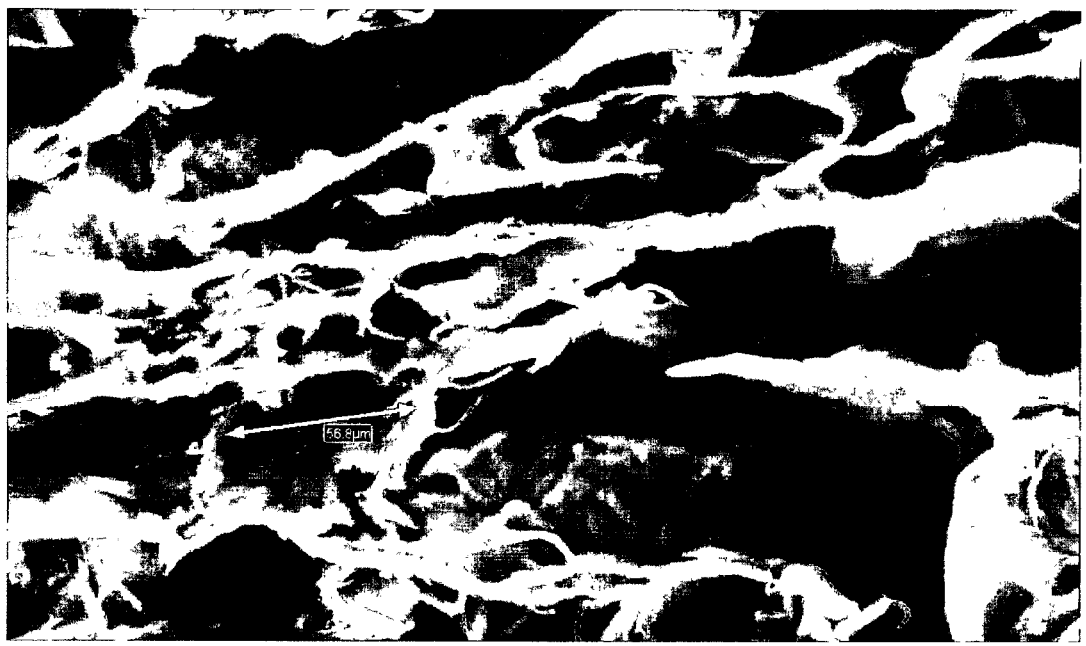
FIG. 4 is an image from a scanning electron microscope which shows a cross-section of a porous reticulated SIS open cell foam scaffold, with an example of a pore indicated by the arrow, the image being at a greater magnification than the images of FIGS. 1-3.
Figure 5:
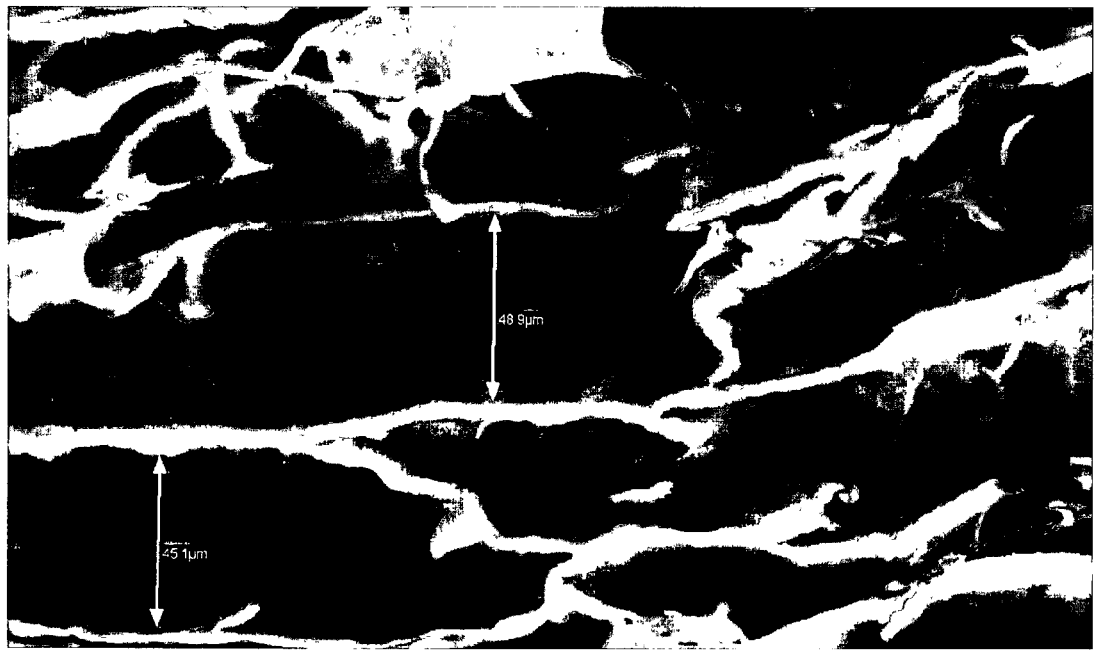
FIG. 5 is an image from a scanning electron microscope which shows a cross-section of a porous reticulated SIS open cell foam scaffold, with examples of pores indicated by the arrows, the image being at a greater magnification than the images of FIGS. 1-3.
Figure 6:
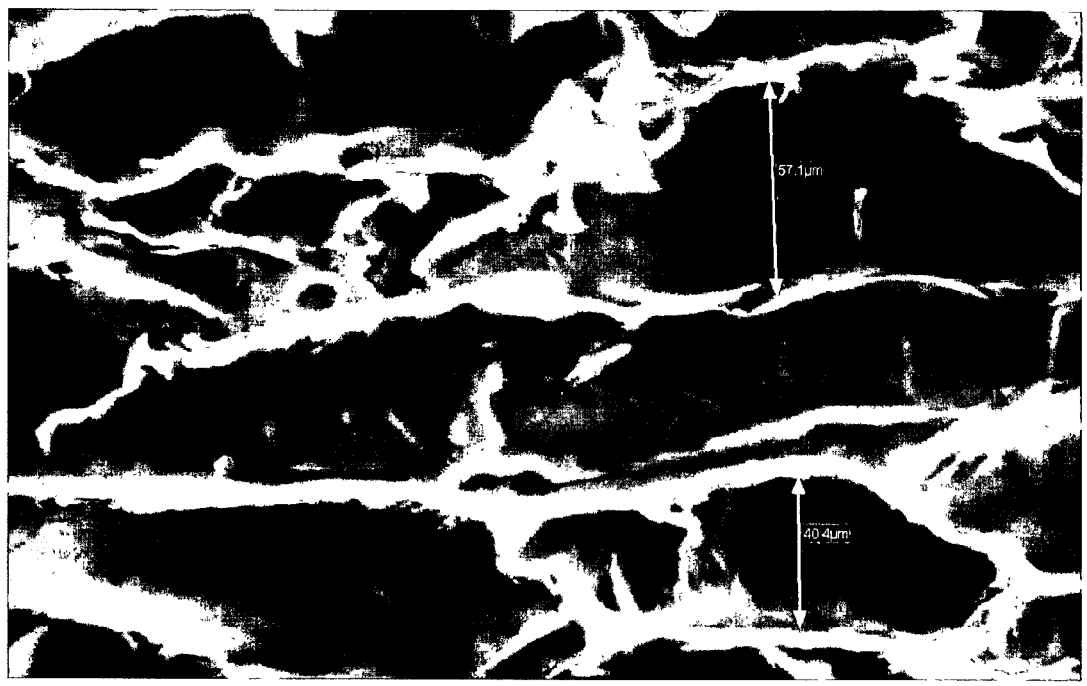
FIG. 6 is an image from a scanning electron microscope which shows a cross-section of a porous reticulated SIS open cell foam scaffold, with examples of pores indicated by the arrows, the image being at a greater magnification than the images of FIGS. 1-3.
Figure 7:
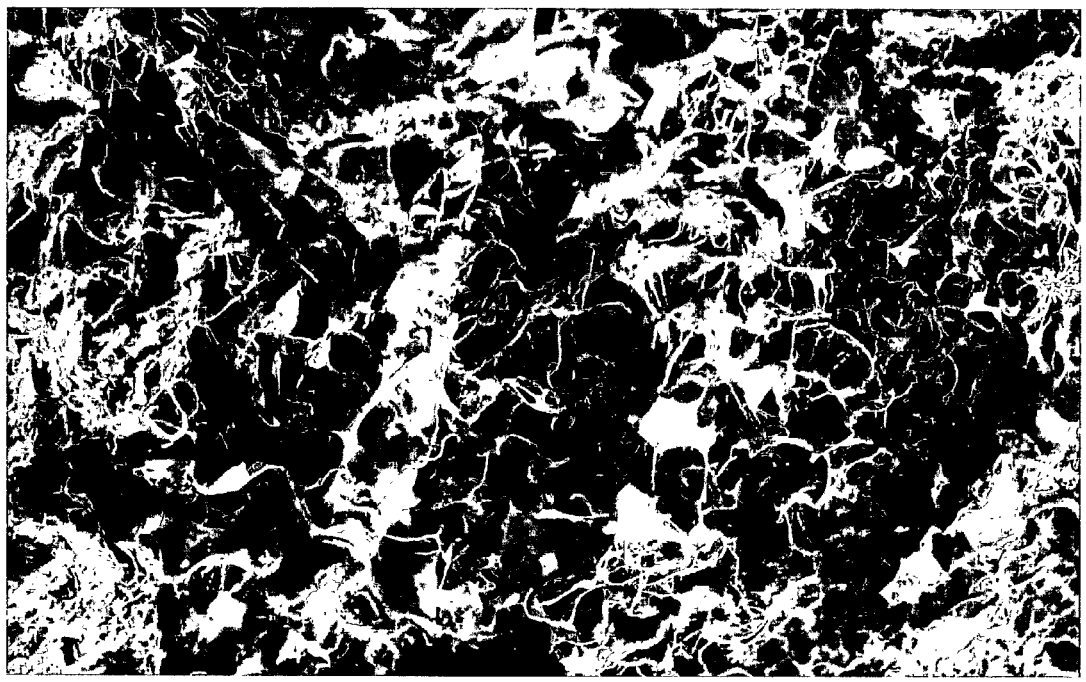
FIG. 7 is an image from a scanning electron microscope which shows a cross-section of a porous reticulated SIS open cell foam scaffold, the image being at a greater magnification than the images of FIGS. 1-3.
Figure 8:
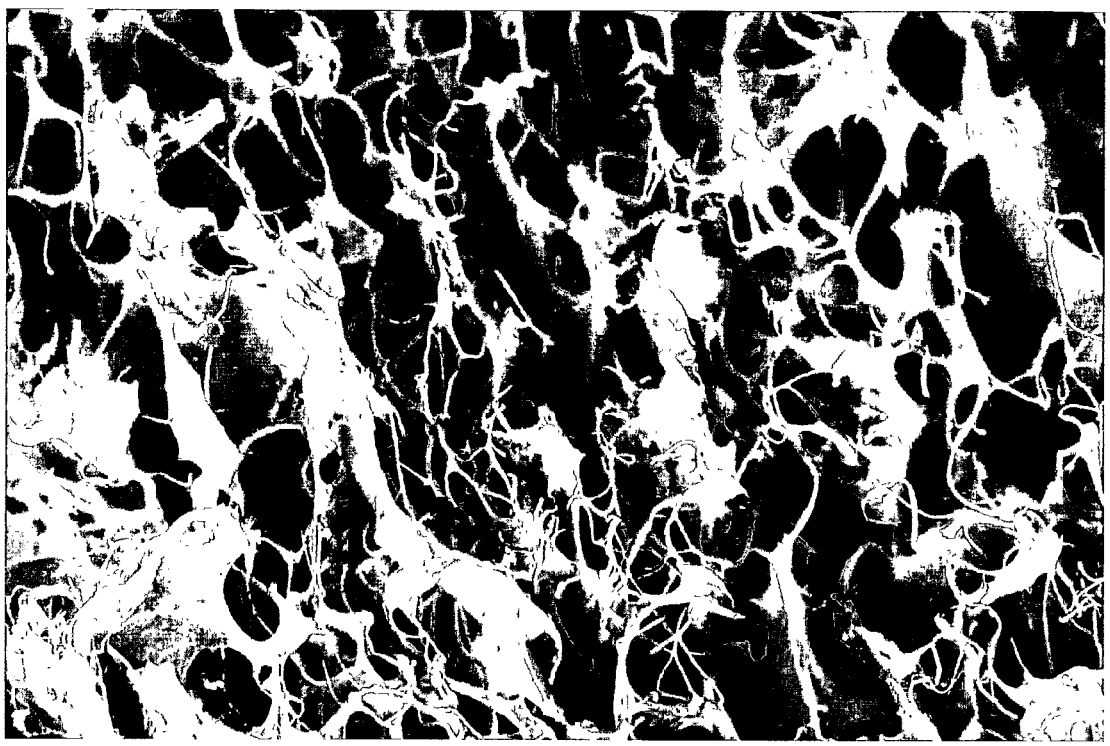
FIG. 8 is an image from a scanning electron microscope which shows a surface of a porous reticulated SIS open cell foam scaffold, the image being at a greater magnification than the images of FIGS. 1-3.

Pore sizes can be determined from scanning electron microscope images of the exterior surface of the foam, as in FIGS. 1-3 and 8, and of cross-sections of the foam, as in FIGS. 4-7. These images may be used in conjunction with standard commercially available image analysis software to determine the ranges of pore sizes. FIGS. 4-6 illustrate the results of using suitable commercially-available software to measure or estimate the pore sizes in the foam. This technique was used to determine that the Example 1 foam had pores in the range of 600-700 microns. The sample may also include smaller pores.

EXAMPLE 2

Example 2 demonstrates the fabrication of a porous SIS scaffold having a relatively moderate pore size and a relatively moderate material density. Such scaffolds are obtained by compacting the comminuted SIS material by centrifugation, freezing at a faster rate (relative to Example 1) and to a lower temperature (i.e., to $-80°$ C.), followed by lyophilization of the resultant mass. The procedure is as follows. First, comminuted SIS is fabricated as described above in regard to Example 1. Specifically, scissor-cut SIS runners (~6" long) is comminuted by two passes through a suitable comminuting machine to produce a "slurry" of SIS material (thin, long SIS fibers ~200 microns thick×1-5 mm long) suspended relatively uniformly in water.

Next, the mass of each of four empty twenty-four well plates is recorded. Under a sterile hood using sterile conditions, an approximately 3 ml aliquot of the comminuted SIS material is placed in each well of the tissue culture plates. The mass of each plate full of material is then recorded.

The plates are then balanced for centrifuging by use of the following technique. The two plates are placed on the balance, and RO water is added to the area in between the wells of the lighter plate until the two plates are balanced. The two plates are then placed across from one another in the centrifuge, and centrifuged at 3000 rpm for seven minutes. Once done, the plates are removed from the centrifuge, and the water is emptied therefrom. The mass of each of the plates is then recorded. The centrifuging and mass measurement process is then repeated for the remaining plates.

The plates are then placed in a −80° C. freezer until the specimen is fully frozen. Depending upon the bulk of the material, the time for full freezing can vary from about 1 to about 30 minutes, for example. The frozen plates are then removed from the freezer and placed in a suitable lyophilization machine and lyophilized under similar parameters to as described above in regard to Example 1 (i.e., for a first period at a primary drying temperature of −13° C. for 8 hours, followed by a second period at a secondary drying temperature of 35° C. for 4 hours).

After the lyophilization cycle is complete, the plates are removed from the lyophilization machine and the mass of each plate is determined and recorded. The results from this process are summarized in the following table:

| Average Volume | Average Mass | Average Density |
|---|---|---|
| 0.285 ml | 0.010104 g | 0.035 (g/cc) |

As with the samples of Example 1, a scanning electron image of the surface of each of the samples prepared in accordance with Example 2 was taken to visualize the relative pore sizes. An image indicative of the samples prepared in accordance with Example 2 is shown in FIG. 2. Using the technique described above for determining pore size, this sample was found to have pores in the range of about 100-150 microns.

EXAMPLE 3

Example 3 demonstrates the fabrication of a porous SIS scaffold having a relatively small pore size and a relatively high material density. Such scaffolds are obtained by compacting the comminuted SIS material to an even higher density than in Example 2, flash-freezing the samples using liquid nitrogen, followed by lyophilization. The procedure is as follows. First, comminuted SIS is fabricated as described above in regard to Examples 1 and 2. Specifically, scissor-cut SIS runners (~6" long) is comminuted by two passes through a suitable comminuting machine to produce a "slurry" of SIS material (thin, long SIS fibers ~200 microns thick ×1-5 mm long) suspended relatively uniformly in water. Once done, the resultant mass is centrifuged under a dead-weight. The dead weights are prepared as follows. Forty-eight strips of 3 M™ COBAN™ Self-Adherent Wrap (commercially available from 3 M™ of St. Paul, MN) are cut into pieces that measure 50 mm in length and 5mm in width (unstretched). COBAN™ Self-Adherent Wrap is a laminate of nonwoven material and elastic fibers placed lengthwise to provide elasticity. The elastic wrap contains a cohesive material that makes it stick to itself but not to other materials or skin. Thereafter, the pieces are stretched and wrapped around the outer edges of a polyethylene disk measuring 1 cm in diameter and 2 mm in thickness. Each strip is trimmed, if need be, so that the COBAN™ Self-Adherent Wrap strips wrap around the disk two times.

Next, the mass of each of four empty twenty-four well plates is recorded. Under a sterile hood using sterile conditions, an approximately 3 ml aliquot of the comminuted SIS material is placed in each well of the tissue culture plates. The mass of each full plate of material is then recorded. The plates are then balanced and centrifuged as described above in regard to Example 2. Thereafter, the water is drained from the plates, and the mass of each of the centrifuged plates is recorded.

Once this is completed, the wells of the plates are combined at a ratio of 2:1 thereby reducing the number of plates from four to two. An attempt is made to combine low material wells with high material wells in order to have a somewhat consistent amount of SIS material in each well. The mass of each full plate is then recorded. The polyethylene disks wrapped with COBAN™ Self-Adherent Wrap are then placed into each well. The two plates are then balanced using the technique described above in regard to Example 2. The plates are then centrifuged at 3000 rpm for five minutes. Thereafter, the plates are removed from the centrifuge, the water is emptied therefrom, and the polyethylene disks are also removed. The mass of each plate is again recorded. The two plates are balanced once again (in a manner similar to as described above in regard to Example 2), and the plates are again centrifuged at 3000 rpm for seven minutes. Once done, the water is emptied again from each of the plates, and the mass of each plate is again recorded.

Contemporaneously with the centrifuging process, a liquid nitrogen bath is prepared by pouring liquid nitrogen into a wide-mouthed liquid nitrogen container. The plates are kept in the centrifuge until the bath is ready. Thereafter, each plate is dipped into the bath and held in the liquid for approximately 15 seconds. Upon removal from the nitrogen bath, the plates are immediately placed in a −80° C. freezer to prevent thawing. The frozen plates are then removed from the freezer and placed in a suitable lyophilization machine and lyophilized under similar parameters to as described above in regard to Examples 1 and 2 (i.e., for a first period at a primary drying temperature of −13° C. for 8 hours, followed by a second period at a secondary drying temperature of 35° C. for 4 hours).

After the lyophilization cycle is complete, the plates are removed from the lyophilization machine and the mass of each plate is determined and recorded. The results from this process are summarized in the following table:

| Average Volume | Average Mass | Average Density |
|---|---|---|
| 0.786 ml | 0.071563 g | 0.091 (g/cc) |

As with the samples of Examples 1 and 2, a scanning electron image of the surface of each of the samples prepared in accordance with Example 3 was taken to visualize the relative pore sizes. An image indicative of the samples prepared in accordance with Example 3 is shown in FIG. 3. Using the technique described above for determining pore size, this sample was found to have pores in the range of about 40-60 microns. Such pore sizes are illustrated in FIGS. 4-6, indicated by the arrows.

As shown in the scanning electron microscope images of FIGS. 1-8, each of the illustrated ECM foams comprises a three-dimensional network of reticulated naturally occurring ECM defining a plurality of interconnected pores. The foam has these pores throughout its height, width, and thickness. The pores are open and interconnected to define a plurality of irregularly-shaped interconnected passageways leading from the exterior surface of the foam (see FIGS. 1-3 and 8) into the interior of the foam (see cross-sections FIGS. 4-7). These interconnected passageways are three-dimensional. As discussed above, the sizes of the pores, and therefore the maximum size for the interconnected passageways, can be controlled by controlling the manufacturing process as described above.

These interconnected passageways facilitate cell migration through the implant and enable efficient nutrient exchange in vivo. These interconnected passageways also provide a means of transmitting bioactive agents, biologically derived substances (e.g. stimulants), cells and/or biological lubricants, biocompatible inorganic materials, synthetic polymers and biopolymers (e.g. collagen) throughout the length, width and thickness of the ECM prior to implantation. The interconnected passageways defined by the pores also serve as passageways for materials used during the manufacturing process, such as compounds used for chemically cross-linking the foam. These interconnected passageways as well as the outer surfaces of the foam may also serve as sites on which the above materials are carried.

As shown in the above examples, the process parameters can be varied to produce an ECM foam that has the desired porosity for the particular application. For example, it may be desirable to produce a foam with lower density (and higher porosity) for applications involving osteocytes and to produce a foam with higher density (and lower porosity) for applications involving chondrocytes.

Moreover, the ECM foams described herein may be crosslinked. Specifically, the ECM foams described herein may be either chemically or physically crosslinked.

As can be seen in the scanning electron microscopic images of FIGS. 1-8, each of the illustrated ECM foams comprises interconnected pieces of naturally occurring extracellular matrix. As shown in the scanning electron microscope images of cross-sections of the ECM foams of FIGS. 4-7, these interconnected pieces of naturally occurring extracellular matrix provide the foam with an interior surface having an three-dimensional topography of irregular shape. As shown in the scanning electron microscope images of the surfaces of the ECM foam, these interconnected pieces of naturally occurring extracellular matrix provide the foam with exterior surfaces having three-dimensional topographies of irregular shapes. With these irregular three-dimensional topographies and the interconnected passageways, the ECM foams of the present disclosure provide a relatively large surface area of naturally occurring ECM. Such a large surface area of naturally occurring ECM can be advantageous in providing a relatively large surface area to which biological agents, biologically derived agents, cells, biocompatible polymers and biocompatible inorganic materials can be affixed pre-implantation. In addition, the illustrated ECM foams provide a relatively large surface of area of naturally occurring ECM to which cells may attach in vivo.

ECM foam products can be made with substantially lower densities than those of other ECM products. For comparison, the density of the commercially available RESTORE® product (DePuy Orthopaedics. Inc. in Warsaw. Ind), an ECM laminate, is 0.466+/−0.074 g/cc. The DePuy product is described for use during rotator cuff surgery. and is provided as a resorbable framework that allows the rotator cuff tendon to regenerate itself. The RESTORE® Implant is derived from porcine small intestine submucosa that has been cleaned. disinfected, and sterilized. An ECM product consisting of comminuted and hardened SIS as described in U.S. patent application Ser. No. 10/195,719 entitled "Devices from Naturally Occurring Biologically Derived Materials", has been made with a density of can be 0.74+/−0.059 g/cc. And, an ECM product consisting of toughened SIS laminate as described in U.S. patent application Ser. No. 10/195,794 entitled "Meniscus Regeneration Device and Method" has been made with a density of 0.933+/−0.061 g/cc.

As discussed above, the ECM foams of the present disclosure may be combined with bioactive agents, biologically derived substances, cells and/or stimulants, biocompatible inorganic materials and/or biocompatible polymers (e.g. biocompatible synthetic polymers and biopolymers) and combinations of two or more of these materials at the time of manufacture. Illustratively, cells can be seeded throughout the three-dimensional volume of the ECM foam; the biological materials can be dried on the ECM foam at manufacture; the biological materials and the ECM foam can be co-lyophilized; and the biological materials can be covalently linked to the ECM foam. It is contemplated to bond, cross-link, or otherwise incorporate one or more of these materials to the raw ECM material prior to formation of the ECM foam. Alternatively, the materials could be bonded, cross-linked, or otherwise incorporated to the final ECM foam after lyophilization. Finally, combinations of the above methods may be used. For example, an implant of covalently linked ECM foam and biological lubricant can be implanted and additional intra-articular injections of the same or different biological lubricants can be made at surgery, post-operatively, or both at surgery and post-operatively.

"Bioactive agents" include one or more of the following: chemotactic agents; therapeutic agents (e.g. antibiotics, steroidal and non-steroidal analgesics and anti-inflammatories, anti-rejection agents such as immunosuppressants and anti-cancer drugs); various proteins (e.g. short chain peptides, bone morphogenic proteins, glycoprotein and lipoprotein); cell attachment mediators; biologically active ligands; integrin binding sequence; ligands; various growth and/or differentiation agents (e.g. epidermal growth factor, IGF-I, IGF-II, TGF-$\beta$ I-III, growth and differentiation factors, vascular endothelial growth factors, fibroblast growth factors, platelet derived growth factors, insulin derived growth factor and transforming growth factors, parathyroid hormone, parathyroid hormone related peptide, bFGF; TGF$_\beta$ superfamily factors; BMP-2; BMP-4; BMP-6; BMP-12; sonic hedgehog; GDF5; GDF6; GDF8; PDGF); small molecules that affect the upregulation of specific growth factors; tenascin-C; hyaluronic acid; chondroitin sulfate; fibronectin; decorin; thromboelastin; thrombin-derived peptides; heparin-binding domains; heparin; heparan sulfate; DNA fragments and DNA plasmids. If other such substances have therapeutic value in the orthopaedic field, it is anticipated that at least some of these substances will have use in concepts of the present disclosure, and such substances should be included in the meaning of "bioactive agent" and "bioactive agents" unless expressly limited otherwise.

"Biologically derived agents" include one or more of the following: bone (autograft, allograft, and xenograft) and derivates of bone; cartilage (autograft, allograft and xenograft), including, for example, meniscal tissue, and derivatives; ligament (autograft, allograft and xenograft) and derivatives; derivatives of intestinal tissue (autograft, allograft and xenograft), including for example submucosa; derivatives of stomach tissue (autograft, allograft and xenograft), including for example submucosa; derivatives of bladder tissue (autograft, allograft and xenograft), including for example submucosa; derivatives of alimentary tissue (autograft, allograft and xenograft), including for example submucosa; derivatives of respiratory tissue (autograft, allograft and xenograft), including for example submucosa; derivatives of genital tissue (autograft, allograft and xenograft), including for example submucosa; derivatives of liver tissue (autograft, allograft and xenograft), including for example liver basement membrane; derivatives of skin tissue; platelet rich plasma (PRP), platelet poor plasma, bone marrow aspirate, demineralized bone matrix, insulin derived growth factor, whole blood, fibrin and blood clot. Purified ECM and other collagen sources are also intended to be included within "biologically derived agents." If other such substances have therapeutic value in the orthopaedic field, it is anticipated that at least some of these substances will have use in the concepts of the present disclosure, and such substances should be included in the meaning of "biologically-derived agent" and "biologically-derived agents" unless expressly limited otherwise.

"Biologically derived agents" also include bioremodelable collageneous tissue matrices. The expressions "bioremodelable collagenous tissue matrix" and "naturally occurring bioremodelable collageneous tissue matrix" include matrices derived from native tissue selected from the group consisting of skin, artery, vein, pericardium, heart valve, dura mater, ligament, bone, cartilage, bladder, liver, stomach, fascia and intestine, tendon, whatever the source. Although "naturally occurring bioremodelable collageneous tissue matrix" is intended to refer to matrix material that has been cleaned, processed, sterilized, and optionally crosslinked, it is not within the definition of a naturally occurring bioremodelable collageneous tissue matrix to purify the natural fibers and reform a matrix material from purified natural fibers. The term "bioremodelable collageneous tissue matrices" includes "extracellular matrices" within its definition.

"Cells" include one or more of the following: chondrocytes; fibrochondrocytes; osteocytes; osteoblasts; osteoclasts; synoviocytes; bone marrow cells; mesenchymal cells; stromal cells; stem cells; embryonic stem cells; precursor cells derived from adipose tissue; peripheral blood progenitor cells; stem cells isolated from adult tissue; genetically transformed cells; a combination of chondrocytes and other cells; a combination of osteocytes and other cells; a combination of synoviocytes and other cells; a combination of bone marrow cells and other cells; a combination of mesenchymal cells and other cells; a combination of stromal cells and other cells; a combination of stem cells and other cells; a combination of embryonic stem cells and other cells; a combination of precursor cells isolated from adult tissue and other cells; a combination of peripheral blood progenitor cells and other cells; a combination of stem cells isolated from adult tissue and other cells; and a combination of genetically transformed cells and other cells. If other cells are found to have therapeutic value in the orthopaedic field, it is anticipated that at least some of these cells will have use in the concepts of the present disclosure, and such cells should be included within the meaning of "cell" and "cells" unless expressly limited otherwise.

"Biological lubricants" include: hyaluronic acid and its salts, such as sodium hyaluronate; glycosaminoglycans such as dermatan sulfate, heparan sulfate, chondroiton sulfate and keratan sulfate; synovial fluid and components of synovial fluid, including as mucinous glycoproteins (e.g. lubricin), vitronectin, tribonectins, articular cartilage superficial zone proteins, surface-active phospholipids, lubricating glycoproteins I, II; and rooster comb hyaluronate. "Biological lubricant" is also intended to include commercial products such as ARTHREASE™ high molecular weight sodium hyaluronate, available in Europe from DePuy International, Ltd. of Leeds, England, and manufactured by Bio-Technology General (Israel) Ltd., of Rehovot, Israel; SYNVISC® Hylan G-F 20, manufactured by Biomatrix, Inc., of Ridgefield, New Jersey and distributed by Wyeth-Ayerst Pharmaceuticals of Philadelphia, Pennsylvania; HYLAGAN® sodium hyaluronate, available from Sanofi-Synthelabo, Inc., of New York, New York, manufactured by FIDIA S.p.A., of Padua, Italy; and HEALON® sodium hyaluronate, available from Pharmacia Corporation of Peapack, New Jersey in concentrations of 1%, 1.4% and 2.3% (for opthalmologic uses). If other such substances have therapeutic value in the orthopaedic field, it is anticipated that at least some of these substances will have use in the concepts of the present disclosure, and such substances should be included in the meaning of "biological lubricant" and "biological lubricants" unless expressly limited otherwise. "Biocompatible polymers" is intended to include both synthetic polymers and biopolymers (e.g. collagen). Examples of biocompatible polymers include: polyesters of [alpha]-hydroxycarboxylic acids, such as poly(L-lactide) (PLLA) and polyglycolide (PGA); poly-p-dioxanone (PDO); polycaprolactone (PCL); polyvinyl alchohol (PVA); polyethylene oxide (PEO); polymers disclosed in U.S. Pat. Nos. 6,333,029 and 6,355,699; and any other bioresorbable and biocompatible polymer, co-polymer or mixture of polymers or co-polymers that are utilized in the construction of prosthetic implants. In addition, as new biocompatible, bioresorbable materials are developed, it is expected that at least some of them will be useful materials from which orthopaedic devices may be made. It should be understood that the above materials are identified by way of example only, and the present invention is not limited to any particular material unless expressly called for in the claims.

"Biocompatible inorganic materials" include materials such as hydroxyapatite, all calcium phosphates, alpha-tricalcium phosphate, beta-tricalcium phosphate, calcium carbonate, barium carbonate, calcium sulfate, barium sulfate, polymorphs of calcium phosphate, ceramic particles, and combinations of such materials. If other such substances have therapeutic value in the orthopaedic field, it is anticipated that at least some of these substances will have use in the concepts of the present disclosure, and such substances should be included in the meaning of "biocompatible inorganic material" and "biocompatible inorganic materials" unless expressly limited otherwise.

It is expected that various combinations of bioactive agents, biologically derived agents, cells, biological lubricants, biocompatible inorganic materials, biocompatible polymers can be used with the scaffolds of the present disclosure.

It is expected that standard sterilization techniques may be used with the products of the present disclosure.

Illustratively, in one example of embodiments that are to be seeded with living cells such as chondrocytes, a sterilized implant may be subsequently seeded with living cells and packaged in an appropriate medium for the cell type used. For example, a cell culture medium comprising Dulbecco's Modified Eagles Medium (DMEM) can be used with standard additives such as non-essential aminoacids, glucose, ascorbic acid, sodium pyrovate, fungicides, antibiotics, etc., in concentrations deemed appropriate for cell type, shipping conditions, etc.

It is anticipated that the ECM foams of the present disclosure may be combined with the concepts disclosed in the following applications for U.S. patent, filed concurrently herewith, which are incorporated by reference herein in their entireties: Ser. No. 10/195,794 entitled "Meniscus Regeneration Device and Method"; Ser. No. 10/195,719 entitled "Devices from Naturally Occurring Biologically Derived Materials"; Ser. No. 10/195,347 entitled "Cartilage Repair Apparatus and Method"; Ser. No. 10/195,344 entitled "Unitary Surgical Device and Method"; Ser. No. 10/195,341 entitled "Hybrid Biologic/Synthetic Porous Extracellular Matrix Scaffolds"; Ser. No. 10/195,606 entitled "Cartilage Repair and Regeneration Device and Method" Ser. No. 10/195,334 entitled "Cartilage Repair and Regeneration Scaffolds and Method"; and Ser. No. 10/195,633 entitled "Porous Delivery Scaffold and Method", along with U.S. patent application Ser. No. 10/172,347 entitled "Hybrid Biologic-Synthetic Bioabsorbable Scaffolds" which was filed on Jun. 14, 2002. For example, for orthopaedic uses, it may be desirable to accompany or follow implantation with a treatment regime involving administering hyaluronic acid to the implantation site.

As can be seen from the forgoing description, the concepts of the present disclosure provide numerous advantages. For example, the concepts of the present disclosure provide for the fabrication of a porous implantable scaffold which may have varying mechanical properties to fit the needs of a given scaffold design. For instance, the pore size and the material density may be varied to produce a scaffold having a desired mechanical configuration. In particular, such variation of the pore size and the material density of the scaffold is particularly useful when designing a scaffold which provides for a desired amount of cellular migration therethrough, while also providing a desired amount of structural rigidity. In addition, according to the concepts of the present disclosure, implantable devices can be produced that not only have the appropriate physical microstructure to enable desired cellular activity upon implantation, but also has the biochemistry (collagens, growth factors, glycosaminoglycans, etc.) naturally found in such ECMs.

Although it is believed that naturally occurring extracellular matrix provides advantages over purified extracellular matrix, it is contemplated that the teachings of the present disclosure can be applied to purified extracellular matrix as well. Thus, it is expected that the naturally occurring extracellular matrix could be purified prior to physically comminuting the extracellular matrix. This purification could comprise treating the naturally occurring extracellular matrix to remove substantially all materials other than collagen prior to physically comminuting the extracellular matrix. The purification could be carried out to substantially remove glycoproteins, glycosaminoglycans, proteoglycans, lipids, non-collagenous proteins and nucleic acids (DNA and RNA).

While the disclosure is susceptible to various modifications and alternative forms, specific exemplary embodiments thereof have been shown by way of example in the drawings and has herein be described in detail. It should be understood, however, that there is no intent to limit the disclosure to the particular forms disclosed, but on the contrary, the intention is to cover all modifications, equivalents, and alternatives falling within the spirit and scope of the disclosure.

There are a plurality of advantages of the present disclosure arising from the various features of the apparatus and methods described herein. It will be noted that alternative embodiments of the apparatus and methods of the present disclosure may not include all of the features described yet still benefit from at least some of the advantages of such features. Those of ordinary skill in the art may readily devise their own implementations of an apparatus and method that incorporate one or more of the features of the present disclosure and fall within the spirit and scope of the present disclosure.

The invention claimed is:

1. A method of making an implantable scaffold for repairing or regenerating body tissue, the method comprising the steps of:
cutting naturally occurring extracellular matrix material in the presence of a liquid to produce a cohesive mass of intertwined strips, ribbons, or fibers; and
freeze drying the cohesive mass to form a porous structure.

2. The method of claim 1, further comprising the step of freezing the cohesive mass to form a frozen composition, said frozen composition comprising ice crystals, the freezing step being performed prior to the freeze drying step.

3. The method of claim 1, wherein the extracellular matrix material comprises material selected from the group consisting of: small intestine submucosa, bladder submucosa, stomach submucosa, alimentary submucosa, respiratory submucosa, genital submucosa, and liver basement membrane.

4. The method of claim 1, further comprising the step of flashfreezing the cohesive mass prior to the freeze drying step.

5. The method of claim 1, further comprising the step of compacting the cohesive mass prior to the freeze drying step.

6. The method of claim 1, further comprising the step of centrifuging the cohesive mass prior to the freeze drying step.

7. The method of claim 1, further comprising the step of freezing the cohesive mass at a controlled rate of temperature drop.

8. A method of making an implantable scaffold for repairing or regenerating body tissue, the method comprising the steps of:
providing a naturally occurring extracellular matrix material selected from the group consisting of: small intestine submucosa, stomach submucosa, bladder submucosa, respiratory submucosa, alimentary submucosa, genital submucosa, and liver basement membrane;
cutting the naturally occurring extracellular matrix material in the presence of a liquid to produce a cohesive mass of intertwined strips, ribbons, or fibers; and
freeze drying the cohesive mass to form a porous structure.

9. A method of making an implantable scaffold for repairing or regenerating body tissue, the method comprising the steps of:
cutting naturally occurring extracellular matrix material in the presence of a liquid to produce a cohesive mass of intertwined strips, ribbons, or fibers,
freezing the cohesive mass at a controlled rate of temperature drop, and
freeze drying the cohesive mass to form a porous structure,
wherein the cohesive mass is frozen by reducing the temperature of the naturally occurring extracellular matrix at a rate of $-1°$ C./min or less.

10. A method of making an implantable scaffold for repairing or regenerating body tissue, the method comprising the steps of:
cutting naturally occurring extracellular matrix material in the presence of a liquid to produce a cohesive mass of intertwined strips, ribbons, or fibers,
freezing the cohesive mass at a controlled rate of temperature drop, and
freeze drying the cohesive mass to form a porous structure,
wherein the cohesive mass is frozen by reducing the temperature of the naturally occurring extracellular matrix at a rate of greater than $-1°$ C./min.

* * * * *